(12) United States Patent
Williams et al.

(10) Patent No.: US 6,800,610 B2
(45) Date of Patent: Oct. 5, 2004

(54) OSTEOCLAST SECRETED CHEMOKINE AND USES THEREOF

(75) Inventors: John P. Williams, Lexington, KY (US); Jay M. McDonald, Birmingham, AL (US); Margaret A. McKenna, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 10/157,457

(22) Filed: May 29, 2002

(65) Prior Publication Data

US 2002/0150568 A1 Oct. 17, 2002

Related U.S. Application Data

(63) Continuation-in-part of application No. 09/884,570, filed on Jun. 19, 2001, now Pat. No. 6,566,333.
(60) Provisional application No. 60/212,271, filed on Jun. 19, 2000.

(51) Int. Cl.$^7$ .......................... A61K 38/00; A61K 38/19
(52) U.S. Cl. .............................. 514/12; 514/2; 424/85.1
(58) Field of Search ........................ 514/12, 2; 424/85.1

(56) References Cited

FOREIGN PATENT DOCUMENTS

KR          97065715 A    * 10/1997

OTHER PUBLICATIONS

Yamada et al. p. 33. an endogenous target protein for arginine–specific ADP–ribosyltransferase in chicken polymorphonuclear leukocytes. is highly homologous to mim–1 protein (myb–induced myeloid protein–1). FEBS Lett. 311:203–205. 1992.*
Swiss–Prot. Accession No. P08940. Jul. 15, 1999.*
Choi et al. A–Geneseq. Accession No AAM152000 Mar. 15, 2002.*
Ness et al. The v–myb oncogene product binds to and activates the promyelocyte–specific mim–1 gene. Cell 59; 1115–1125. 1989.*

* cited by examiner

*Primary Examiner*—Gary Kunz
*Assistant Examiner*—Ruixiang Li
(74) *Attorney, Agent, or Firm*—Benjamin Aaron Adler

(57) ABSTRACT

The present invention demonstrates the biological function of a newly identified osteoclast-secreted protein. This protein, mim-1, has sequence homology with but is distinct from a previously identified neutrophil chemokine protein. Mim-1 may be a key signaling protein secreted by osteoclasts that regulates recruitment and/or differentiation of osteoblast and osteoclast precursor cells. This protein may also serve to maintain osteoclasts in a relatively inactive state prior to secretion. This mechanism is essential for regulating the mass and structural integrity of bone. This protein or an analog and/or antagonists of this protein will have potential therapeutic potential in the treatment of a variety of pathological bone diseases including osteoporosis and metastatic bone diseases.

2 Claims, 25 Drawing Sheets

```
1    MPALSLIALL  SLVSTAFARQ  WEVHPPQQQG  RHWAQICSGN
41   PFNRIRGCDR  YGCGNYGASR  QGKGEKHKGV  DVICTDGSIV
81   YAPFSGQLSG  PIRFFHNGNA  IDDGVQISGS  GYCVKLVCIH
121  PIRYHGQIQK  GQQLGRMLPM  QKVFPGIVSH  IHVENCDQSD
161  PTHLLRPIPD  ISPPFPQQDA  HWAVVCAGNP  TNEIRGCDKY
201  GCGYFGAPRR  NGKGEKHKGV  DVICADGATV  YAPFSGELSG
241  PVKFFHNGNA  IDDGVQIRGS  GFCVKLLCIH  PIRYNGRISK
281  GQVLGRMLPM  QRVFPGIISH  IHVENCDRSD  PTSNLERGKG
321  ESEMEV    (SEQ ID. NO 8)
```

Fig. 3A

```
38  YGCGQYSAQR TQRHHP- GV DVLCSDGSVV YAPFTGKIVG 77  Lect2
51  YGCGNYGASR QGKGEKHKGV DVICTDGSIV YAPFSGQLSG 90  mim N
200 YGCGYFGAPR NGKGEKHKGV DVICADGATV YAPFSGELSG 239 mim C 78  QEKPYRNKMA INDGIRLSGR GFCVKIFYIK PIKYKGSIKK 117 Lect2
91  PIRFFHNGNA IDDGVQISGS GFCVKLLCIH PIRYNGRISK 130 mim N
240 PVKFFHNGNA IDDGVQIRGS GYCVKLVCIH PIRYHGQIQK 279 mim C 118 GEKLGTLLPL QKIYPGIQSH VHVENCDSSD PTAYL 152 Lect2 (SEQ ID NO. 12)
131 GQVLGRMLPM QRVFPGIISH VHVENCDSSD PTAYL 165 mim N  (SEQ ID NO. 13)
280 GQQLGRMLPM QKVFPGIVSH IHVENCDQSD PTHLL 315 mim C  (SEQ ID NO. 14)
```

Fig. 3B

OSTEOCLAST SECRETED CHEMOKINE AND USES THEREOF

CROSS REFERENCE TO RELATED APPLICATION

This non-provisional patent application is a continuation-in-part application of non-provisional application U.S. Ser. No. 09/884,570, filed Jun. 19, 2001, issued as U.S. Pat. No. 6,566,333, which claims priority benefit of provisional patent application U.S. Serial No. 60/212,271, filed Jun. 19, 2000, now abandoned.

FEDERAL FUNDING LEGEND

This invention was produced in part using funds obtained through a grant from the National Institutes of Health. Consequently, the federal government has certain rights in this invention.

BACKGROUND OF THE INVENTION

1. Field of the Invention

The present invention relates generally to the fields of biochemical endocrinology and regulation of bone formation and degradation. More specifically, the present invention relates to the regulation of osteoblast function by the osteoclast secreted chemokine-like protein mim-1 and uses thereof.

2. Description of the Related Art

Osteoclasts are multinucleated cells formed by fusion of precursors derived from pleuripotential hematopoietic stem cells (1) that circulate in the monocyte fraction (2, 3). Differentiation of the precursors into osteoclasts is a complex process that requires both M-CSF and RANKL (ODF, osteoclast differentiation factor; also known as TRANCE) (4, 5). The mechanism(s) by which osteoclastic precursors are recruited to an area of bone resorption, establish and differentiate into mature osteoclasts is a complex process that is still not fully understood.

Mature osteoclasts are terminally differentiated cells and while it is clear that M-CSF and RANKL are essential for differentiation of osteoclasts, additional osteoclast-inductive agents or synergistic effectors of RANKL are likely to be important in the development of active mature osteoclasts (6, 7). In fact, RANKL/TRANCE is not bone-specific since it was first cloned as a tumor necrosis factor (TNF) related activation-induced cytokine (TRANCE) in T-cell hybridomas suggesting a potential role in immune function (8).

Communication, via a variety of signaling molecules, has long been proposed as a key component in the homeostatic signaling process between osteoclasts and osteoblasts (9, 10). Osteoclasts respond to numerous factors that are derived from bone or the bone microenvironment including, among others, IL-1, IL-6, TNF-α and TGF-β and osteoprotegrin (6, 7, 10–13). Under conditions of normal bone turnover, bone resorption is followed by new bone synthesis. The mechanisms regulating recruitment of osteoblast precursors into areas recently degraded are poorly understood, but presumably involve a signaling pathway between osteoclasts and osteoblasts (14).

The prior art is deficient in methods of regulating the secretion of a chemokine-like protein expressed specifically by cells of hematopoietic origin, like osteoclasts, so as to manipulate a signaling pathway that may be involved in regulating recruitment of osteoblast precursor cells to areas of recent bone resorption b y osteoclasts. The present invention fulfills this long-standing need and desire in the art.

SUMMARY OF THE INVENTION

Mim-1 is a protein reported to be expressed specifically by cells of hematopoietic origin (15), which includes osteoclasts. Mim-1 is distinct from, but homologous with, the neutrophil chemokine protein, LECT2, and is an abundant protein in osteoclasts. In addition, mim-1 is secreted in a time dependent manner in vitro. Furthermore, secretion of mim-1 is stimulated in a PMA concentration dependent manner. Secretion of mim-1 precedes the largest increase in PMA stimulated bone resorption by isolated osteoclasts. Immunofluorescence microscopy demonstrated that both avian osteoclasts and human osteoclast-like cells but not mesenchymal stem cells (which includes osteoblast precursors) express mim-1. Mim-1 may be a key signaling protein secreted by osteoclasts that regulates recruitment and/or differentiation of osteoblast precursor cells, thereby providing an essential mechanism for regulating the mass and structural integrity of bone.

The present invention is drawn to methods of inducing recruitment and proliferation of osteoblasts, increased bone resorption by osteoclasts and decreased differentiation of osteoclast precursor cells following secretion or administration of mim-1. Generally, the mim-1 protein has the sequence of SEQ ID NO. 8 or a fragment thereof.

In another aspect of the present invention, there is provided methods of inducing bone resorption activity of osteoclasts, inducing recruitment and proliferation of osteoblasts, and inducing new bone synthesis in an individual by mim-1 protein. Generally, the mim-1 protein has the sequence of SEQ ID NO. 8 or a fragment thereof.

In yet another aspect of the present invention, there is provided a method of stimulating bone marrow cell differentiation in an individual by a mim-1 protein. Generally, the mim-1 protein has the sequence of SEQ ID NO. 8 or a fragment thereof.

In one more aspect of this invention, there is provided a pharmaceutical composition comprising mim-1 protein in a pharmaceutically acceptable vehicle. Generally, the mim-1 protein has the sequence of SEQ ID NO. 8 or a fragment thereof.

In a further aspect of the present invention, there is provided a method of inhibiting cancer cell growth in an individual with a pharmaceutical composition comprising mim-1 protein in a pharmaceutically acceptable vehicle, where mim-1 protein generally has the sequence of SEQ ID NO. 8 or a fragment thereof.

In a still further aspect of the present invention, there is provided a polyclonal antibody against and specifically binds to mim-1 protein, a pharmaceutical composition comprising the polyclonal antibody in a pharmaceutically acceptable vehicle and a method to inhibit excessive bone synthesis in an individual with the pharmaceutical composition comprising the polyclonal antibody in a pharmaceutically acceptable vehicle. Generally, mim-1 protein generally has the sequence of SEQ ID NO. 8 or a fragment thereof.

In yet a further aspect of the invention, there is provided a recombinant mim-1 gene which produces mim-1 antisense mRNA that hybridizes to endogenous mim-1 mRNA and inhibiting expression of endogenous mim-1, a vector expressing recombinant mim-1 gene, a host cell comprising the vector expressing recombinant mim-1 gene and a method to inhibit excessive bone synthesis in an individual with the vector expressing recombinant mim-1 gene.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 10 shows immunocytochemical staining of mim-1 in developing mouse limb buds. Immunocytochemical staining with the mim-1 polyclonal antibody was performed on 18.5 day mouse embryo saggital sections. (FIGS. 10B and 10C at 80×).

FIG. 11 shows immunocytochemical localization of mim-1 in developing murine cranium. Immunocytochemical staining with the mim-1 polyclonal antibody was performed on 18.5 day mouse embryo saggital sections.

FIG. 13 shows Northern analysis of osteoclast and osteoblast RNA for mim-1 expression. RNA denaturing gel for total RNA from chicken osteoclasts (OC), human stromal cells (SC), and MG63 cells.

FIG. 17 shows the time and concentration dependent effects of mim-1 on cbfa1 binding to osteocalcin cbfa1 promoter binding sites.

FIG. 18 shows mim-1 stimulates vitamin D receptor binding to the VDRE in the absence of added ligand.

DETAILED DESCRIPTION OF THE INVENTION

Figure 1:
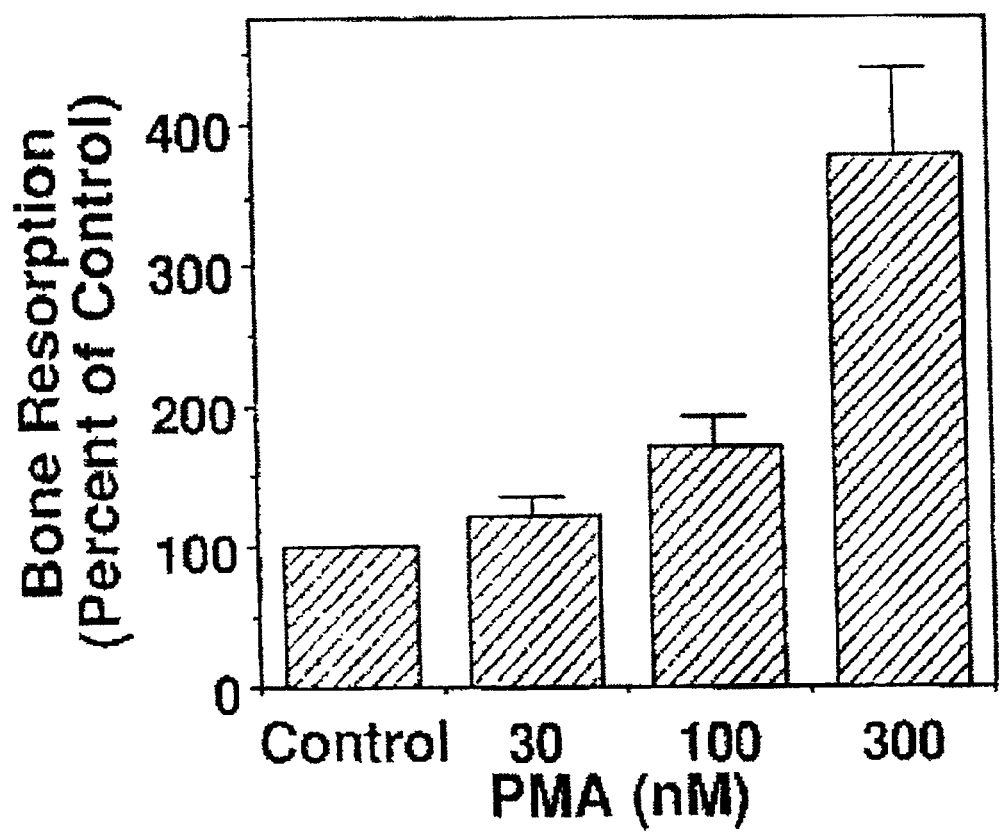
FIG. 1 shows the effect of PMA on osteoclastic bone resorption. Bone resorption assays using 150 μg labeled bone were cultured for four days in the presence of increasing concentrations of PMA. Resorption activity was quantified by measuring $^3$H proline released to the media. Data represent the mean +/−SEM of n=5 experiments each performed in quadruplicate.

The following abbreviations may be used herein: PMA, phorbol myristate acetate: Mim-1, myb induced myeloid protein-1; PBS, phosphate buffered saline; TRAP, tartrate resistant acid phosphatase; EGTA; ethylene glycol-bis(β-aminoethylether) N, N', N'-tetraacetic acid, EDTA, ethylenedinitrilo tetraacetic acid; NaF, sodium fluoride; PMSF, phenylmethylsulfonylfluoride; SDS-PAGE, sodium dodecylsulf ate-polyacrylamide gel electrophoresis; PVDF, polyvinylidine difluoride; BSA, bovine serum albumin.

Osteoclasts are terminally differentiated cells of hematopoietic origin. Phorbol myristate acetate stimulates bone resorption 4-fold with a simultaneous dose dependent increase in calmodulin protein levels. Phorbol myristate acetate treatment of osteoclasts also results in a dramatic decrease in a 35 kD protein in osteoclast lysates detected by Coomassie staining. The decrease in 35 kD protein correlates with increases in bone resorption. Peptide digests of the protein were analyzed by HPLC/MS/MS and provided sequence data from 7 peptides. Sequence analysis indicates that the protein is myb induced myeloid protein-1 precursor (mim-1 protein) based on sequencing 104 of 326 amino acids. Mim-1 is expressed specifically by cells of hematopoietic origin, has an internal repeat sequence of 136 amino acids, no known function and is reported to be a secreted protein. Mim-1 is homologous with Lect2, a neutrophil chemokine, which also stimulates proliferation of osteoblasts. Western analysis demonstrated that the PMA dependent decrease in mim-1 in osteoclasts is due to the protein being secreted into culture media. Immunofluorescence studies demonstrate that mim-1 is localized with a cytoplasmic and perinuclear distribution, in both avian osteoclasts and human osteoclast-like cells. Expression and secretion of a chemokine-like protein suggests a possible, osteoclast derived, signaling pathway that may be involved in coordinating bone remodeling.

The present invention is drawn to methods of inducing recruitment and proliferation of osteoblasts, increased bone resorption by osteoclasts and decreased differentiation of osteoclast precursor cells following secretion or administration of mim-1. Generally, the mim-1 protein has the sequence of SEQ ID NO. 8 or a fragment thereof.

In another aspect of the present invention, there is provided methods of inducing bone resorption activity of osteoclasts, inducing recruitment and proliferation of osteoblasts, and inducing new bone synthesis in an individual by mim-1 protein. Generally, the mim-1 protein has the sequence of SEQ ID NO. 8 or a fragment thereof.

In yet another aspect of the present invention, there is provided a method of stimulating bone marrow cell differentiation in an individual by a mim-1 protein. Generally, the mim-1 protein has the sequence of SEQ ID NO. 8 or a fragment thereof.

In one more aspect of this invention, there is provided a pharmaceutical composition comprising mim-1 protein in a pharmaceutically acceptable vehicle. Generally, the mim-1 protein has the sequence of SEQ ID NO. 8 or a fragment thereof.

In a further aspect of the present invention, there is provided a method of inhibiting cancer cell growth in an individual with a pharmaceutical composition comprising mim-1 protein in a pharmaceutically acceptable vehicle, where mim-1 protein generally has the sequence of SEQ ID NO. 8 or a fragment thereof.

In a still further aspect of the present invention, there is provided a polyclonal antibody against and specifically binds to mim-1 protein, a pharmaceutical composition comprising the polyclonal antibody in a pharmaceutically acceptable vehicle and a method to inhibit excessive bone synthesis in an individual with the pharmaceutical composition comprising the polyclonal antibody in a pharmaceutically acceptable vehicle. Generally, mim-1 protein generally has the sequence of SEQ ID NO. 8 or a fragment thereof.

In yet a further aspect of the invention, there is provided a recombinant mim-1 gene which produces mim-1 antisense mRNA that hybridizes to endogenous mim-1 mRNA and inhibiting expression of endogenous mim-1, a vector expressing recombinant mim-1 gene, a host cell comprising the vector expressing recombinant mim-1 gene and a method to inhibit excessive bone synthesis in an individual with the vector expressing recombinant mim-1 gene.

The following examples are given for the purpose of illustrating various embodiments of the invention and are not meant to limit the present invention in any fashion:

EXAMPLE 1
Isolation and Culture of Osteoclasts

Avian osteoclasts (from egg-laying white Leghorn hens) were utilized because gram quantities of pure osteoclasts are readily obtained. Avian osteoclasts (>$10^7$ cells) were isolated as previously described (16). Laying hens on a limited calcium diet produce massive numbers of osteoclasts to meet the calcium requirement for eggshell production. The endosteum of such birds, is >50% osteoclasts by mass. Medullary bone is scraped from the endosteum into calcium- and magnesium-free phosphate-buffered saline (PBS) a t 4° C. Cells are separated from matrix by washing through 100 $\mu$m nylon filters and sedimented through 70% newborn calf serum. Osteoclasts purified by density gradient sedimentation, result in preparations in which osteoclasts represent ~75–90% of viable cells. Following sedimentation, macrophages represent <2% of the cell mass. For experiments requiring homogeneous osteoclasts the cells purified by serum sedimentation are then affinity purified b y attachment to bone fragments and then resedimented 24 hrs later, eliminating essentially all but viable, bone-attached osteoclasts (17).

EXAMPLE 2
Human Osteoclast-Like Cell Differentiation

Human blood monocytes were isolated by plasma pheresis from healthy volunteers. Human blood monocytes ($1 \times 10^5$ cells/well) are cultured in the presence of 90% confluent MG63 cells in Minimal Essential Media-$\beta$ containing 10% fetal bovine serum, $10^{-7}$ M dexamethasone, and $10^{-8}$ M 1, 25 dihydroxy vitamin $D_3$. Differentiation to TRAP positive cells was used as a marker for the osteoclast phenotype (not illustrated). In parallel experiments cells were plated at a similar density on 18×18 mm cover slips and immunostained for mim-1.

EXAMPLE 3
Preparation of Devitalized-[$^3$H]-Proline Labeled Bone

L-[$^3$H]-proline-labeled devitalized bone is used as substrate in the avian osteoclast resorption assay. This substrate has the advantages of reflecting removal of both the mineral and organic phases of bone, and is resistant to artifacts due to physicochemical exchange (e.g., media acidification (16)). Weanling rats (40–60 g) are injected with 1 mCi of L-[2,3,4,5-$^3$H]-proline, >100 Ci/mmol, on alternate days for 10 days. Rats are sacrificed on day 12 and bone recovered by dissection. After washing, the bone is dried in a desiccator at 42° C. for 7 days. Labeled 20–40 $\mu$m bone fragments are obtained by grinding the bone in a ball bearing mill and sieving to size.

EXAMPLE 4
Bone Resorption Assays

Osteoclasts are plated at 2–3×$10^3$ cells/well on 24 well plates with 100 $\mu$g of labeled 20–40 $\mu$m $^3$H labeled bone fragments. To avoid possible contamination (due to fusing macrophages or growth of fibroblast/osteoblast cells) bone resorption is measured after 4 days. Osteoclasts rapidly (~4 hrs) attach to and begin to degrade the bone fragments, releasing label into the media. Bone degradation is determined by measuring label released to the media. Comparison of the $^3$H proline release and pit assays give comparable results (17, 18). The $^3$H proline assay is also resistant to pH-dependent artifacts and has less inter-assay variability than pit assays (17–19). Activity, with 100 µg bone fragments, is linear over 5–7 days (16).

EXAMPLE 5
Osteoclast Lysis and Western Analysis

Avian osteoclasts are washed with phosphate buffered saline (PBS) and lysed as previously described (20). The lysis buffer (Buffer A) is 50 mM Tris, pH 7.0, 250 mM sucrose, 1 mM EGTA, 1 mM EDTA, 1 mM ammonium molybdate, 50 mM NaF, 1 mM orthovanadate, 0.5 µM okadaic acid, 5 mM benzamidine, 0.1 mM PMSF, 0.05 mg/ml pepstatin, 0.06 mg/ml leupeptin, 0.018 trypsin inhibitor units of aprotinin/ml, 10% glycerol and 1% Triton×100. Cells were solubilized 1 hr with rotation and the Triton insoluble material removed by centrifugation at 15,000×g for 5 min at 4° C. Lysates (25 µg protein) were resolved on 10% SDS-PAGE. Protein was transferred under standard conditions (21) to PVDF membranes. Mim-1 was detected on Western analysis using a polyclonal antibody generated against a trpE-mim-1 fusion protein (15) (generously provided by Scott Ness, University of N. Mex.) by enhanced chemiluminescence. Protein concentrations were determined by the Bio Rad DC assay (Bio Rad, Richmond, Calif.).

EXAMPLE 6
Methods for Protein Sequencing

High quality water was prepared using a Millipore (Bedford, Mass.) Milli-Q reagent grade water system. HPLC grade acetonitrile was purchased from Burdick and Jackson (Muskegon, Wis.). Sequencing Grade trifluoroacetic acid (TFA) was purchased from Pierce (Rockford, Ill.). Reagent grade ammonium bicarbonate was purchased from Mallinckrodt (St. Louis, Mo.). Iodoacetic acid was purchased from Sigma (St. Louis, Mo.), and dithiothreitol was purchased from Aldrich (Milwaukee, Wis.). Sequencing grade modified trypsin was purchased from Promega (Madison, Wis.).

EXAMPLE 7
In-Gel Reduction/Alkylation and Digestion

Separated proteins were reduced, alkylated, and digested in-gel using a procedure based on published methods (22, 23). Gel pieces were finely diced and de-stained by multiple 40 minute extractions with 200 mM $NH_4HCO_3$ in 50% acetonitrile at 30° C. Destained gel pieces were dried in a vacuum centrifuge, then rehydrated with 10 mM dithiothreitol and reduced for 1 hour at 56° C. After reduction, the proteins were alkylated with 100 mM iodoacetic acid for 30 minutes, in the dark, at room temperature. Reaction products were removed by rinsing twice with 200 mM $NH_4HCO_3$, followed by twice shrinking the gel with acetonitrile and re-swelling it with 200 mM $NH_4HCO_3$. The gel pieces were dried in a vacuum centrifuge and re-swelled with 50 µg/ml trypsin in 100 mM $NH_4HCO_3$ (prepared by mixing equal volumes of a stock solution of 100 µg/ml trypsin in 1 mM HCl with 200 mM $NH_4HCO_3$). The gel pieces were covered with 200 mM $NH_4HCO_3$ and incubated overnight at 30° C. The reaction was quenched with 2 µl of 10% TFA followed by removal of the supernatant. The gel pieces were twice extracted with 100 µl 0.1% TFA in 60% acetonitrile. The combined extracts and supernatant were taken to near dryness in a vacuum centrifuge and stored frozen until analyzed.

EXAMPLE 8
Microcapillary HPLC/MS/MS Analysis

Protein digests were analyzed using a custom built microcapillary HPLC coupled to a Finnigan MAT LCQ Quadrupole Ion Trap Mass Spectrometer (24). Separations were carried out using 150 µm (inner diameter) porous polymer monolithic columns (25). Data were generated using the Finnigan triple play data-dependent analysis, in which an ion identified in a full mass range scan is scanned at high resolution to determine its appearance mass and charge state and then fragmented to give a tandem (MS/MS) mass spectrum. Instrument parameters were: 210° C. heated metal capillary temperature, 1.10 kV spray voltage, and 35% relative collision energy. Spectra were collected with 2 microscans and a $5 \times 10^7$ automatic gain control target for full scans, 5 microscans and $1.5 \times 10^6$ automatic gain control target for zoom (high resolution) scans, and 8 microscans and $1 \times 10^7$ automatic gain control target for MS/MS scans. MS/MS spectra were searched against the OWL non-redundant database using the Sequest (26) program. Sequest results were confirmed by manually comparing observed and predicted fragmentation patterns for the identified peptides.

EXAMPLE 9
Mim-1 Immunofluorescence Microscopy

Osteoclasts were cultured on 18×18 glass cover slips with or without 20–40 µm bone fragments. Cells were washed with ice cold phosphate buffered saline (PBS), fixed in 3% formaldehyde and permeabilized with 100% methanol for 30 mim at −20° C. Nonspecific binding was blocked with 1% BSA in PBS at 23° C. for 15 minutes. Mim-1 polyclonal antibody (rabbit serum) or nonimmune serum was diluted 1:1000 in blocking buffer and incubated on cover slips for 1 hour at 23° C. Cover slips were washed 4 times for 15 minutes each with PBS and blocked again with blocking buffer. Secondary antibody (FITC conjugated) was diluted 1:1000 and incubated on the cover slips for an hour at 23° C. in the dark. Cover slips were Hoescht stained (20 µg/ml) for 1 hour (for nuclear localization). Cover slips were mounted in 0.1% phenylenediamine in 90% glycerol/PBS. Fluorescence microscopy was performed on a Leica Wetzler microscope attached to a Power MacIntosh computer running IP Lab 3.2 software.

EXAMPLE 10
Immunochemical Staining 18.5 day mouse embryo saggital sections were used. The developing mouse limb buds of mouse embryos were immunostained for mim-1 with mim-1 polyclonal antibody. Mim-1 antibody was diluted 1:500 and incubated for one hour. The slides were washed 4 times and probed with secondary antibody conjugated to diaminobenzidine (DAB) diluted 1:1000. Slides were counterstained with methyl green to show nuclei.

Similar immunochemical staining was performed in developing murine cranium.

EXAMPLE 11
Reverse-Transcriptase Polymerase Chain Reaction (RT-PCR)

To determine whether osteoblasts or osteoblast precursors express mim-1, RT-PCR was performed of human stromal cells as well as derived osteoblasts MG63 (FIG. 12). [This technique is much more sensitive than Northern analysis. Mim-1 was not detected in any of the osteoblastic cell lines. This data strongly suggests that osteoblastic cells, regardless of degree of differentiation, do not express mim-1.]

EXAMPLE 12

Northern Blot Analysis

In view of the strong periosteal staining observed in FIGS. 10 and 11, Northern analysis was performed with 30 μg of total RNA from osteoclasts, stromal cells and MG63 cells (FIG. 13).

Figure 13A:
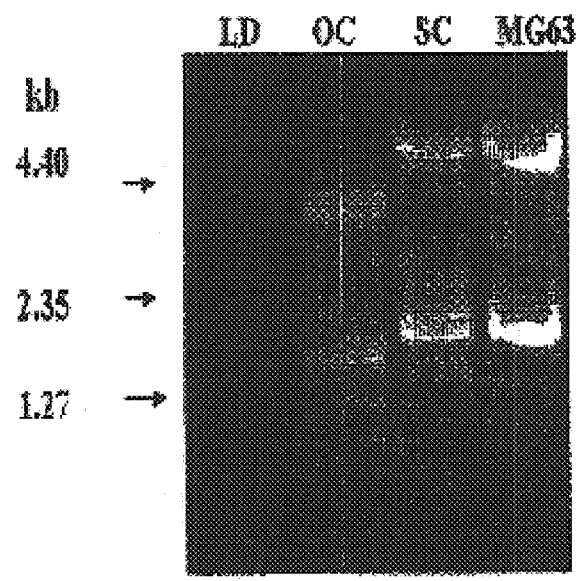
FIG. 13A shows RNA ladder (LD) and avian osteoclast RNA run as control.
Figure 13B:
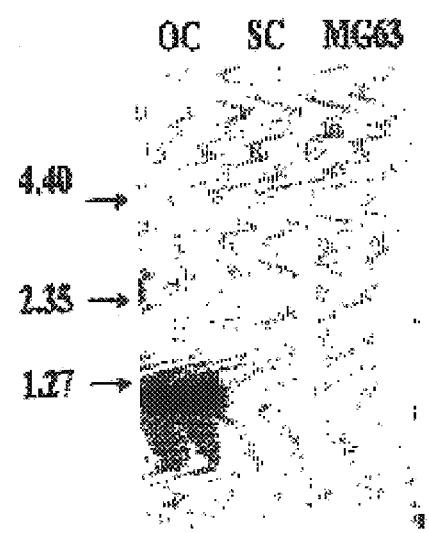
FIG. 13B shows RNA of osteoclasts, human stromal cells, and MG63. RNA from FIG. 13A was transferred to nylon membrane, mim-1 probe was labeled and hybridized with the membrane. Mim-1 mRNA is only detectable in osteoclasts.

Mim-1 is specifically expresses by cells of hematopoietic origin (15). To confirm that mim-1 is readily detected in osteoclast RNA but not in osteoblastic RNA, the above Northern Blot analysis was performed. The mim-1 probes used for RT-PCR amplified product from avian and human sources, therefore arguing against species differences affecting hybridization efficiency in the Northern analysis (FIG. 13). FIG. 13A shows that the human 18 and 28S ribosomal subunits have a slightly different mobility on the gel compared to avian RNA (FIG. 13A) and yet with apparently greater amounts of RNA in the human RNA (FIG. 13A, SC and MG63 compared to OC). FIG. 13B shows that mim-1 was not detected.

EXAMPLE 13

Effects of mim-1 on cbfa1 Binding to Osteocalcin cbfa1 Promoter Binding Sites Cells were treated with 2 μg/ml of purified mim-1 for 0, 10, 30, 60, 120, and 240 min, washed, lysed and nuclear extracts prepared. A 27 bp oligonucleotide from the osteocalcin proximal cbfa1 binding site was 5' end labeled with $^{32}$P-ATP by T4 kinase. Equivalent amounts of nuclear extracts were incubated with the probe for 30 min and samples resolved on a 5% gel, fixed, dried and binding visualized by autoradiography for specific binding.

Similarly, cells were treated with 0, 0.02, 0.3 and 2.0 μg/ml of mim-1 for 2 hrs and mobility shifts done as discussed.

EXAMPLE 14

Effects of mim-1 on Unliganded Vitamin D Receptor Binding to the VDRE

Double stranded oligonucleotide probe, corresponding to the VDRE from the human osteocalcin promoter, is $^{32}$P-labeled with T4 kinase and incubated with nuclear extracts from MG-63 cells treated with 2 μg/ml of mim-mim-1 for 0, 10, 30, 60 and 120 minutes, respectively. Vitamin D receptor interaction was displaced competitively by 100× of cold probe. The cells were then treated with mim-1 for 2 to 3 hrs and VDR/VDRE supershifted with a 1:5 or 1:10 dilution of VDR polyclonal antibody 4707. Competitive displacement with cold probe and incubaton with 100× vitellogenin estrogen response element as a non-specific probe were included as controls with 2 hr mim-1 extracts. VDR/VDRE from MG63 cells was compared to recombinant VDR heterodimer (rVDRhd).

EXAMPLE 15

Effects of mim-1 on in Vitro Matrix Mineralization by MC3T3-E1 Cells

MC3T3-E1 cells, seeded at 2.5×10$^4$ cells/well, were cultured in DMEM/F12 plus 1% FBS in the presence of 10 mM glycerophosphate, 50 μg/ml ascorbic acid and either 0, 3 or 15 nM of purified mim-1 for 16 days. The cells were VonKossa stained to demonstrate a mineralized matrix. VonKossa staining was confirmed by measuring total calcium in each well. The calcium was acid hydrolyzed, neutralized and measured on a Kodak Ektachem DTSC II.

EXAMPLE 16

Effects of mim-1 on Colony Formation by Human Bone Marrow Cells

Human bone marrow cells were cultured in IMDM with GM-CSF (50 ng ml), IL3 (10 ng/ml) and 20 ng/ml SCF (controls) for 3 days with or without 2 μg/ml mim-1. The cells were analyzed by FACS analysis. The remaining cells mim-1 were cultured in colony formation assays an additional 14 days with the same growth factors with or without 2 μg/ml mim-1.

EXAMPLE 17

Mim-1 Inhibition of Human Cancer Cell Lines

Three cancer cell lines (A549, lung cancer; MDA231, breast cancer; and AD10, ovarian cancer) were cultured for three days in the presence of 0 (control), 0.5, 1, 2 and 4 μg/ml of mim-1. Cells were counted in 10 random grids, and the data is plotted as Percent of Control (no added mim-1).

EXAMPLE 18

Results

Figure 2:
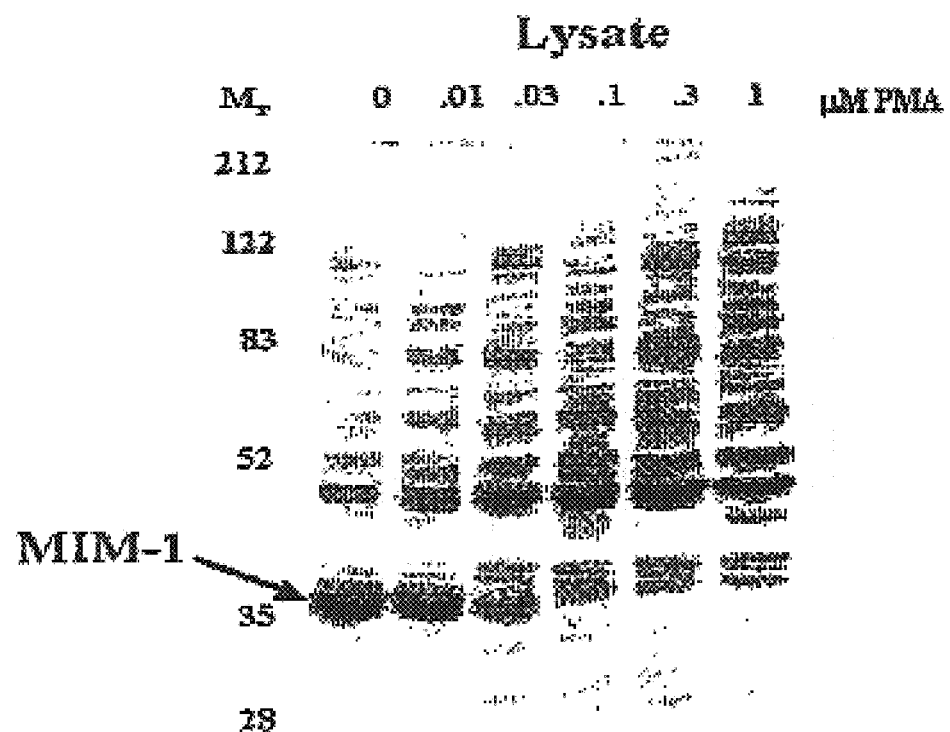
FIG. 2 shows the PMA concentration-dependent decrease in 35 kD osteoclast protein from cell lysates. Bone resorption assays using 150 μg labeled bone were cultured for four days in the presence of increasing concentrations of PMA as described in FIG. 1. Osteoclasts were washed with ice-cold phosphate buffered saline, lysed and 25 μg cell lysates resolved on 10% SDS-PAGE, stained, destained and gels dried. Dried gels were scanned on a UMAXS-12 scanner and the mim-1 protein band is shown. Data are representative of five experiments.

The phorbol ester, PMA, stimulates bone resorption by isolated osteoclasts 4-fold with a $K_{0.5}$ between 0.1 and 0.3 μM (FIG. 1). The PMA-concentration dependent increase in bone resorption was paralleled by a decrease in a 35 kD protein in osteoclast cell lysates as visualized on Coomassie stained gels (FIG. 2). This protein is the lowest molecular weight of three abundant proteins migrating between 35 and 40 kD on SDS-PAGE. The concentration of the 35 kD protein decreases dramatically in response to PMA while the relative abundance of the other two proteins in this region do not change with respect to Coomassie staining.

Figure 3C:
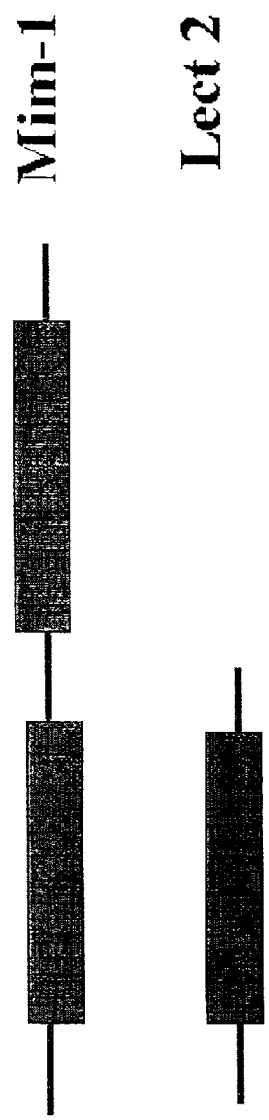
FIG. 3 shows the sequence analysis of 35 kD osteoclast protein. Protein was tryptically digested from gel slices and peptides were resolved by HPLC (FIG. 3A) and sequenced. The full-length amino sequence of mim-1 is shown (FIG. 3B) and amino acids identified by sequence analysis are illustrated in bold. Some of the peptides had over-lapping sequence so that only five peptides are apparent. Repeat sequences from the N and C terminal ends of the protein are aligned with the homologous protein Lect2 (FIG. 3C).

This protein, being one of the most abundant proteins in solubilized osteoclast lysates, was alkylated, reduced, tryptically digested and sequenced from excised gel slices and unambiguously identified as Chicken Myeloid Protein 1 (15, NCBI identifier P08940) or mim-1 (myb induced myeloid protein-mim-1) as described above. Briefly, Coomassie stained bands were excised from gels post-transfer (reducing the number of potential background proteins) and tryptically digested (FIG. 3). Tryptic peptides were resolved by HPLC (FIG. 3A). Seven distinct peptides comprising 31.9% of the complete sequence were identified by tandem mass spectrometry (SEQ ID NO:1–7). One of the peptides identified included the amino acid at position 297, which is the site of a sequence conflict, and was found to be isoleucine rather than tyrosine. No other proteins were identified in the gel band containing the myeloid protein, with the exception of the regularly observed minor contaminant, human keratin. Sequence obtained includes 104 amino acids (FIG. 3B) of the 326 amino acids in the full length sequence reported in original cloning and sequence paper (15). The sequenced peptides obtained are illustrated in FIG. 3B in bold in the full-length sequence of mim-1 (SEQ ID NO: 8).

Examination of the sequence demonstrates that there is a repeat sequence of approximately 136 amino acids in each half of the protein joined by a 14 amino acid "linker". There is high sequence homology between the repeat sequences of mim-1 and the neutrophil chemokine protein, Lect2 (also known as chondromodulin II). The repeat sequences of mim-1 and Lect2 are aligned and illustrated in bold print in FIG. 3C (SEQ ID NO: 9–11). In this repeat structure there are 99 amino acids that are identical and most of the non-identical sites are conservative substitutions. This protein has no known function but was reported to be a secreted protein (15).

Figure 4:
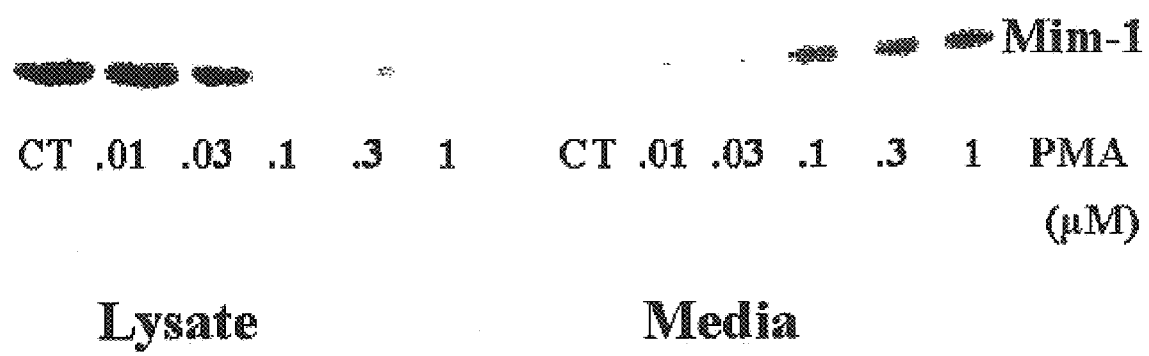
FIG. 4 shows that mim-1 is secreted by osteoclasts in a PMA concentration-dependent manner. Avian osteoclasts were cultured as described in FIGS. 1 and 2; cells were washed with ice cold PBS and lysed. Culture media was collected from each treatment and boiled in sample buffer. Protein (25 μg) from cell lysates (Lysates) and equal aliquots of the corresponding media (Media) were resolved on 10% SDS-PAGE, transferred to PVDF membrane and Western blotted for mim-1. Molecular weights (kilodaltons) are indicated on the left. Representative of n=2 separate experiments.
Figure 5:
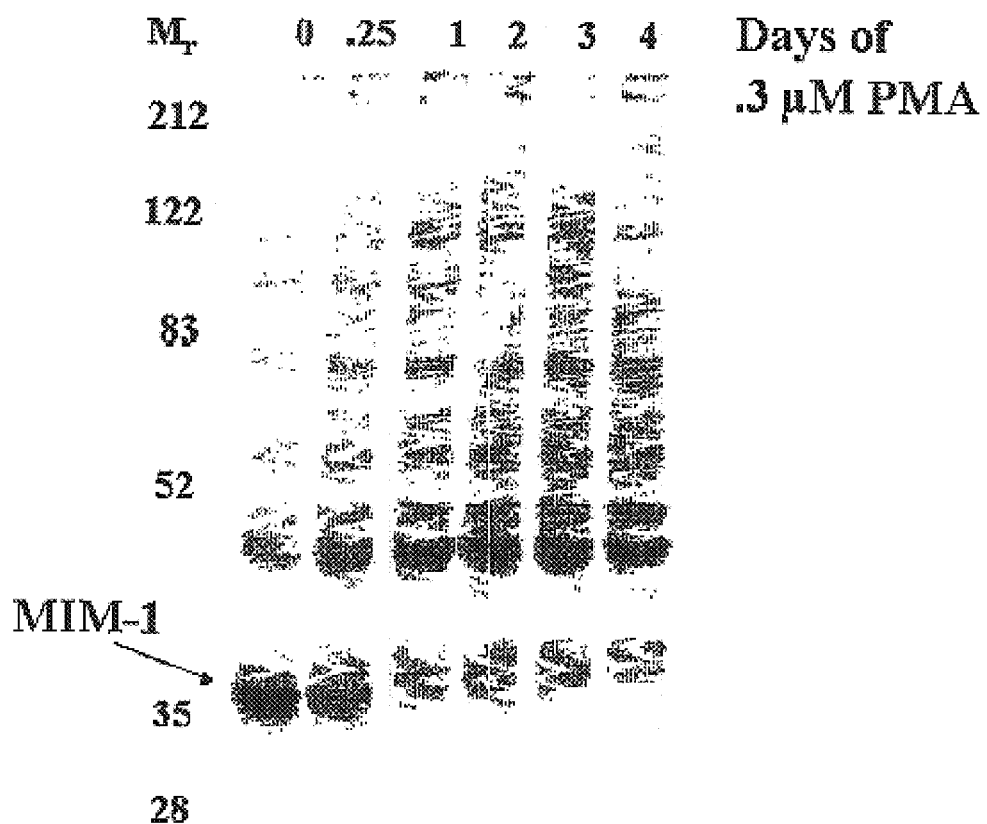
FIG. 5 shows the PMA time-dependent secretion of mim-1. Avian osteoclasts were cultured with bone (1 mg/well) for the indicated times in the presence of 0.3 μM PMA. Osteoclasts were washed with ice-cold phosphate buffered saline, lysed and 25 μg cell lysates resolved on 10% SDS-PAGE, transferred to PVDF membrane and probed with for mim-1 as described in the legend to FIG. 4. Data is representative of two separate experiments.

To determine the effects of PMA on osteoclast secretion of mim-1 and its relation to bone resorption, osteoclasts were cultured as described above in the presence of the indicated concentrations of PMA and aliquots of media removed at the indicated times (FIG. 4) and the level of mim-1 determined by Western analysis. As bone resorption was stimulated (see FIG. 1), mim-1 dercreased in the cell lysate (FIG. 4, left, Lysates) and increased in the culture, media (FIG. 4, right, Media). It is also evident from these data that osteoclasts have a blasal rate of secretion of mim-1 that is independent of PMA treatment. To show that PMA stimulates rapid secretion of mim-1, osteoclasts were treated with 0.3 μM PMA for the indicated times and mim-1 secretion was monitored by Western analysis (FIG. 5).

Figure 6:
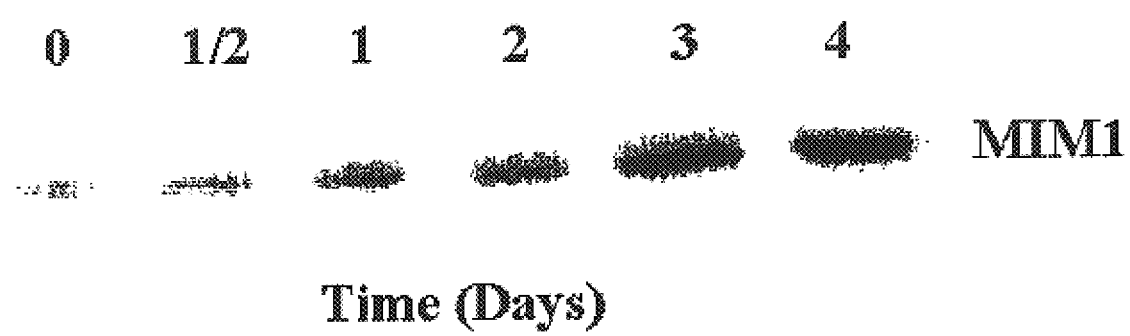
FIG. 6 shows that osteoclasts secrete mim-1 in a time dependent manner independent of PMA. Osteoclasts were cultured with 1 mg of bone as described above in the absence of PMA and aliquots of media removed at the indicated times, samples were resolved on 10% SDS-PAGE, transferred to PVDF membrane and the level of mim-1 determined by Western analysis. Data is representative of two separate experiments performed in duplicate.
Figure 7:
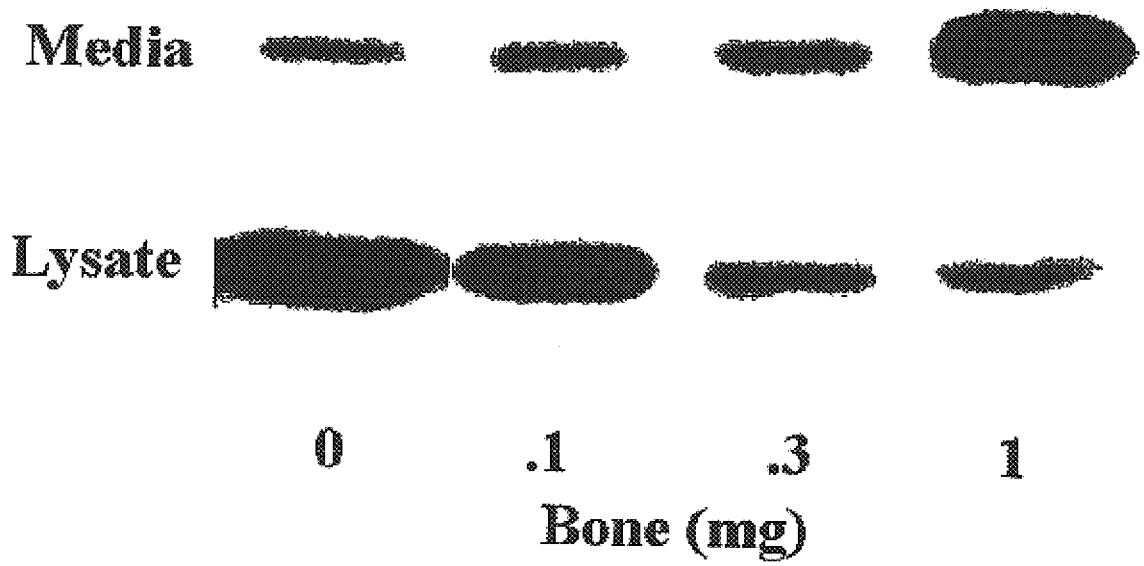
FIG. 7 shows that mim-1 secretion increases as more osteoclasts resorb bone. Osteoclasts were cultured with the indicated concentrations of bone in culture. Bone concentration dependent secretion of mim-1 into culture media was monitored by Western analysis, as was the corresponding concentration-dependent decrease in mim-1 from the osteoclast cell lysates. This data indicates that osteoclasts secrete mim-1 in response to increased bone resorption activity independent of PMA. Data is representative of four experiments.

Osteoclasts secrete mim-1 independent of PMA as demonstrated by culturing osteoclasts on bone for the indicated times and monitoring mim-1 secretion (FIG. 6). Levels of mim-1 increase throughout the 4-day time course. Mim-1 is substantially reduced in cell lysates by 24 hours treatment with PMA (FIG. 5). The time dependence and PMA independence suggests that mim-1 is a signaling protein in bone that appears to be related to bone resorption. This would be logical for an osteoclast-secreted chemokine involved in recruiting osteoblasts. Mim-1 is secreted by osteoclasts actively resorbing bone (FIG. 7). Osteoclasts were cultured with increasing concentrations of bone and mim-1 secretion was monitored by Western analysis as described above. Mim-1 secretion into the media is paralleled by a bone concentration dependent decrease in mim-1 in the osteoclast lysates.

Figure 8A:
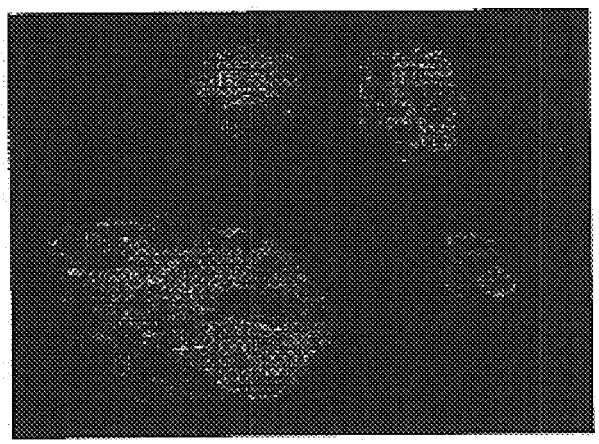
FIG. 8 shows the immunofluorescence localization of avian osteoclast mim-1. Osteoclasts were cultured without bone on 18×18 mm mm cover slips. Cells were incubated in the absence (FIG. 8A and FIG. 8C) or presence (FIG. 8B and FIG. 8D) of 1 μM PMA for 48 hrs. Cells were washed with ice cold PBS, fixed, permeabilized, Hoescht stained for nuclear localization (blue color) and probed with mim-1 (FIG. 8A and FIG. 8B) or non-immune rabbit serum (FIG. 8C and FIG. 8D). Data are representative of three separate experiments.
Figure 8B:
Figure 8C:
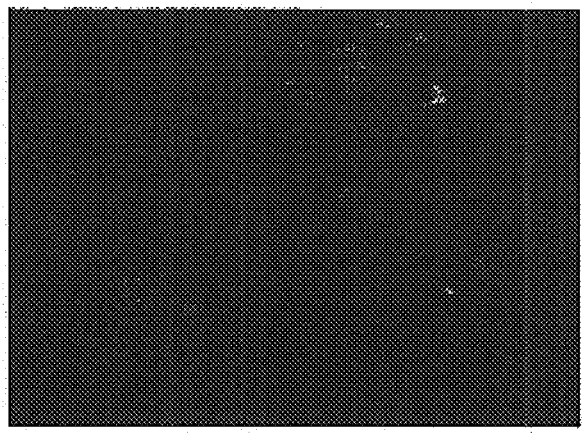
Figure 8D:
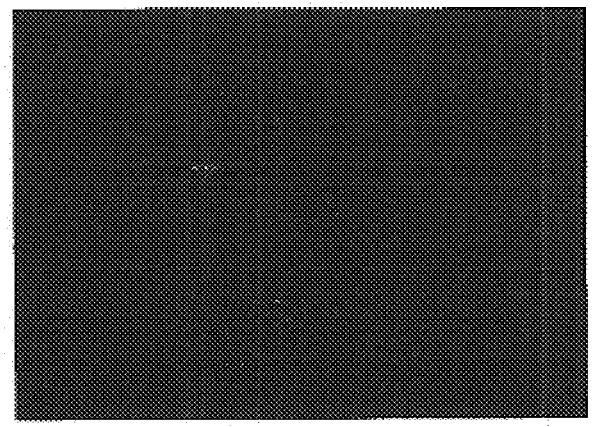
Figure 9A:
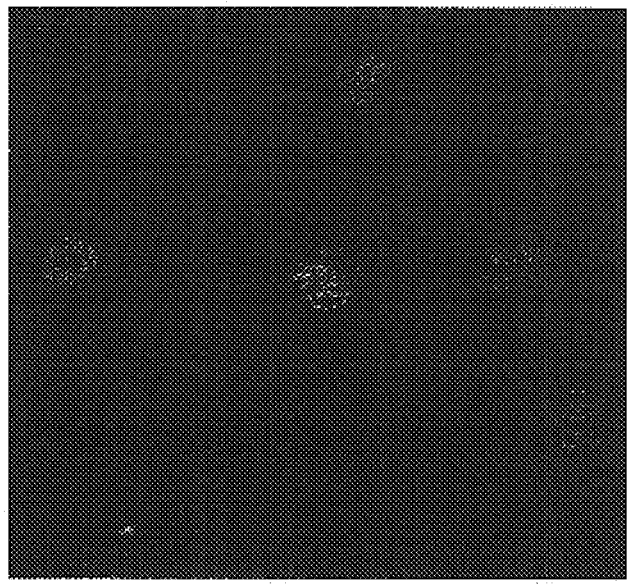
FIG. 9 shows that human osteoclast-like cells express mim-1. Human blood monocytes (5×10$^4$ cells) were co-cultured for 10 days in the presence of MG63 cells (5×10$^5$ cells) in the presence of 10$^{-8}$ M 1, 25 dihydroxy vitamin D3, and 25 ng/ml M-CSF. Cells were Hoescht stained for nuclear localization (blue color) and fluorescence labeling performed as described in the legend to FIG. 8 with mim-1 antibody (FIG. 9A) or nonimmune serum (FIG. 9B). Data are representative of two experiments.

Mim-1 is expressed in bone marrow promyelocytes (15), and is secreted by osteoclasts (FIGS. 2, 4–7) and has been previously been reported to be localized within granules in granulocytes. Immunohistochemistry shows that mim-1 is present in both avian osteoclasts (FIG. 8) and human osteoclast-like cells derived from human blood monocytes (FIG. 9). Osteoclasts were Hoechst stained to show nuclei and mim-1 was localized by immunofluorescence microscopy with FITC labeled secondary antibody with mim-1 or non-immune rabbit serum used as probe. In avian osteoclasts, mim-1 fluorescence is localized in the cytosol and has a perinuclear pattern in osteoclasts. The fluorescence intensity decreased dramatically in response to PMA treatment (FIGS. 8A and 8C), consistent with the observation that osteoclasts secrete mim-1 to the media. Mim-1 in PMA treated osteoclasts appears to be within granules, similar to the distribution reported in promyelocytes (15). Mim-1 staining is specific since in both control and PMA treated osteoclasts fluorescence background with the nonimmune antibody is substantially lower (compare FIGS. 8A, 8B, 8C and 8D, respectively) than with mim-1 antibody indicating the fluorescence.

Figure 9B:
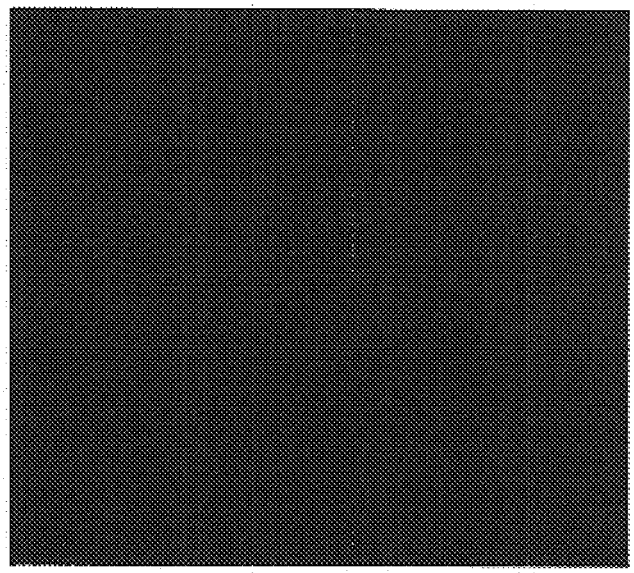

Mim-1 is also present in the human blood monocyte osteoclast-like precursor cells (FIG. 9A) while cells treated with non-immune serum are negative (FIG. 9B). In these experiments the plane of focus is at the level of the blood monocytes, which are above the MG63 cells. Consequently, the nuclei of the MG63 cells are out of the plane of focus and appear dark blue rather than bright blue as in the monocytes. Numerous monocytes have begun to fuse as can be seen by the presence of bi-nucleate cells.

In addition, mim-1 is present in the mouse marrow macrophage differentiation model. In fact, mim-1 effectively blocks osteoclast-like cell differentiation by inhibiting attachment of these cells in the presence of M-CSF and soluble RANKL.

Figure 10A:
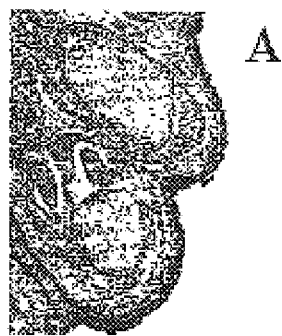
FIG. 10A shows hematoxylin and eosin stain of the forelimb bud (X40).
Figure 10B:
FIG. 10B shows prominent immunohistochemical localization of mim-1 (arrow pointing at periosteal localization) in comparison to nonimmune serum (FIG. 10C)
Figure 10C:
Figure 10D:
FIG. 10D shows mim-1 prominently localized in the periosteal membrane (arrows; 500×). The nuclear localization in chondiocytes seen in FIG. 10D is nonspecific binding since it is also evident in high magnifications of nonimmune controls (not illustrated). Slides were counter-stained with methyl green to show nuclei. Data are representative of three separate experiments.

The immunohistochemical localization of mim-1 in embryonic mice is examined to verify the bone localization. It is readily apparent that mim-1 is localized in areas of new bone growth because of the strong localization of mim-1 in the periosteal membranes of embryonic bones (FIG. 10). The bones developing in the distal terminal region of the fore-limb is shown in hematoxylin and eosin stain (FIG. 10A, 40× magnification). Immunohistochemical localization of mim-1 is prominent (FIG. 10B) in comparison to nonimmune serum (FIG. 10C, both B and C are 80× magnification). The white inset box shown in FIG. 10B is shown in FIG. 10D, 500× magnification, and illustrates that mim-1 is prominently localized in the periosteal membrane. It is also evident that mim-1 is localized in the developing marrow space (FIG. 10B, black arrow).

Figure 11A:
FIG. 11A shows mim-1 localized prominently along suture lines (80×, white square).
Figure 11B:
FIG. 11B shows the white square area of FIG. 11A at 500× magnification.
Figure 11C:
FIG. 11C shows the nonimmune control for FIG. 11A. Nonspecific localization in chondrocytes is evident even at this lower magnification. Immune detection is the same as described in FIG. 10.

In addition, cranial development, which is also proceeding rapidly at 18.5 days, demonstrates that mim-1 is also localized in cranial sutures where cranial plates will fuse (FIG. 11). Mim-1 is heavily localized along suture lines (indicated by white square) in the developing cranial plates (FIG. 11A), which is more clearly delineated in a higher magnification (FIG. 11B). A nonimmune control is shown for comparison (compare FIGS. 11A and 11C). These data (FIGS. 10 and 11) are most likely explained either by periosteal membranes having cells of hematopoietic origin or that mim-1 expression is not specific for cells of hematopoietic origin and is expressed in osteoblastic precursor cells or early in osteoblast differentiation. As mim-1 has been shown to be an osteoclast-secreted protein, the latter seems unlikely. Localization of a primitive hematopoietic cell in the periosteal membrane may be a mechanism to recruit osteoblastic precursor cells to the site of bone growth. It is not possible to determine The lineage of these cells from this data has not been determined.

Figure 12:
FIG. 12 RT-PCR demonstrated mim-1 in an osteoclast cDNA library and mRNA but failed to detect mim-1 in any osteoblast cell lines. This shows that mesenchymal cells (osteoblast precursors) as well as MC3T3-E1 osteoblast precursors and MG63 osteoblast-like cells do not express mim-1 while mim-1 is present in avian osteoclast RNA and is also detected in an osteoclast cDNA library. Lane one represents the mim-1 PCR product amplified from a human osteoclast cDNA library. Lanes 2–5, respectively, shows RNA denaturing gel for total RNA from chicken osteoclasts, human stromal cells, MC3T3-E1 cells and MG63 cells. LD is the RNA ladder. Bands were made negative for reproduction.

To determine whether osteoblasts or osteoblast precursors express mim-1, RT-PCR of human stromal cells as well as derived osteoblasts MG63 were performed (FIG. 12). This technique is likely to be much more sensitive than Northern analysis and mim-1 product was not detected in any of the osteoblastic cell lines. This data, while not conclusive, strongly argues against osteoblastic cells expressing mim-1, regardless of degree of differentiation.

Mim-1 is expressed specifically by cells of hematopoietic origin (15). To verify the accuracy of this information in view of the strong periosteal staining observed in FIGS. 10 and 11, Northern blot analysis was performed with 30 μg of total RNA from osteoclasts, stromal cells and MG63 cells (FIG. 13). Mim-1 is readily detected in osteoclast RNA while mim-1 was not detected in RNA from any of the osteoblastic cells. The mim-1 probes used for RT-PCR amplifies product from avian and human sources, therefore taking into consideration species differences affecting hybridization efficiency in the Northern analysis (FIG. 13). The human 18 and 28S ribosomal subunits have a slightly different mobility on the gel compared to avian RNA (FIG. 13A) and yet with apparently greater amounts of RNA in the human RNA (FIG. 13A, compare SC and MG63 to OC), mim-1 is not detected (FIG. 13B).

Figure 14:
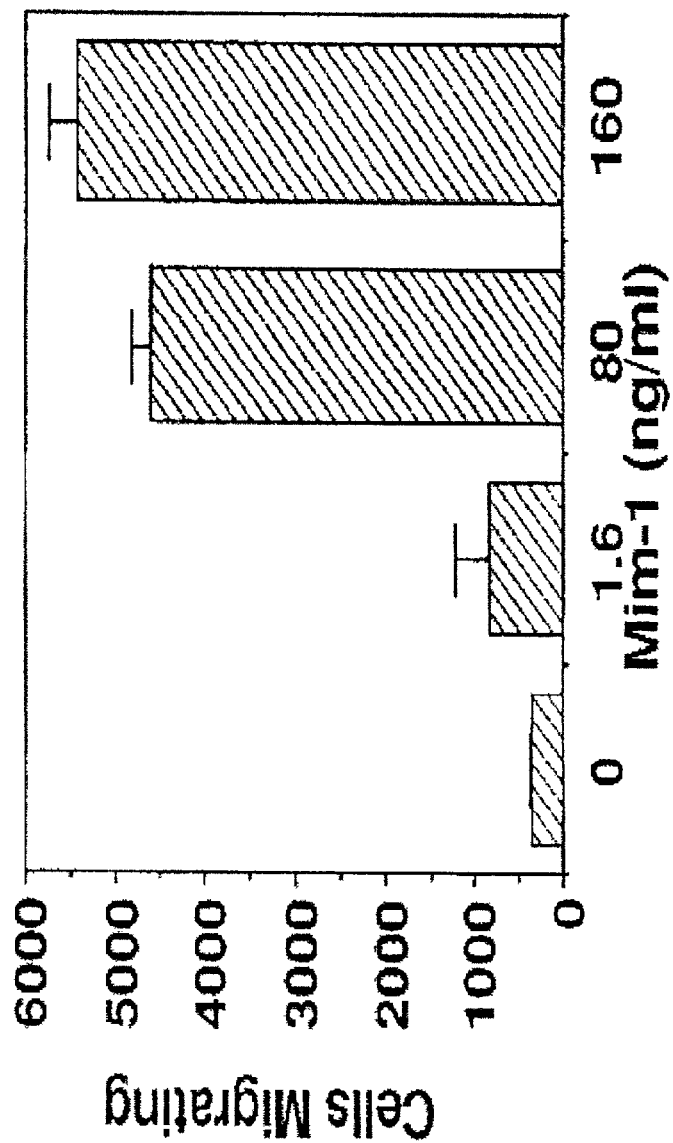
FIG. 14 shows mesenchymal stem cells (osteoblast precursors) migrate to mim-1 in a concentration dependent manner. Mesenchymal stem cells were loaded in the presence of 5 µM calcein in αMEM, and the cells washed twice with media. Cells were plated at 10,000 cells/well in the upper well of Neuroprobe transwell plates. The concentration dependence of mim-1 in migration assays was determined in the transwell migration assay with the indicated concentrations of mim-1 in the bottom chamber. Cells were cultured for 4 hours at 37° C. in a humidified chamber with 5% $CO_2$. Remaining cells were scraped from the upper well and removed. Migration was measured on a fluorescence plate-reader which measures fluorescence in the bottom well and migration was quantified by comparisons with a standard curve generated by serial dilutions of calcein loaded cells plated directly in the bottom chamber. Data is from a single experiment performed in quadruplicate.

To examine if mim-1 regulates recruitment of osteoblast precursors cells, migration assays were performed on mesenchymal stem cells. FIG. 14 shows mesenchymal stem cell migration to purified mim-1 (purified from the GST-mim-1 fusion protein) in a concentration dependent manner, with maximal effects at approximately 100 ng/ml. It is clear that purified mim-1 (cleaved from the GST-mim-1 fusion protein) is biologically active and stimulated precursor cell migration. Mim-1 has no effect on cell proliferation at concentrations up to 2 μg/ml, suggesting that mim-1 may serve to attract osteoblast precursor cells to an area that is newly resorbed, thereby providing a mechanism for coordinating bone remodeling.

Figure 15:
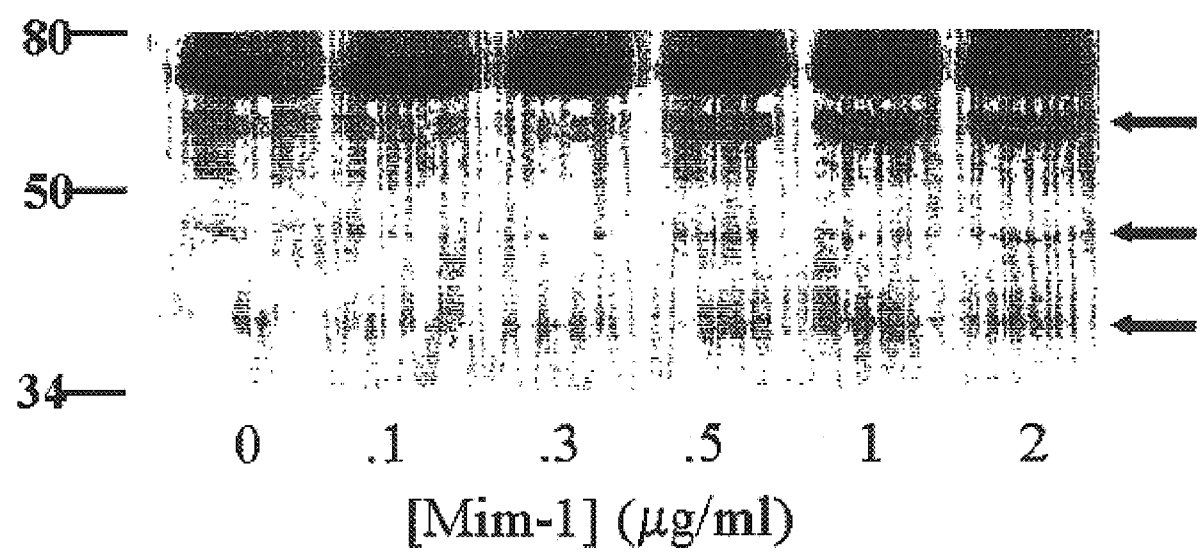
FIG. 15 shows the effect of purified mim-1 on tyrosine phosphorylation in mesenchymal cells. Cells were treated with the indicated concentrations of mim-1 for 3 minutes, washed, lysed and 25 µg protein was resolved on 10% SDS PAGE. Protein w as transferred to PVDF membrane and the membranes probed with phosphotyrosine antibody (4G10 clone; United Biotechnology Incorporated) diluted 1:1000. Data are representative of three separate experiments.

In view of the stimulatory effect of mim-1 on cell migration, the role of mim-1 in modulating signal transduction osteoblast precursor cells (MG63) was examined. Cells were treated with the indicated concentrations of purified mim-1 for 3 minutes, washed and lysed as previously described (20). Equivalent protein (25 µg) was resolved on 10% SDS PAGE, protein transferred to PVDF membrane and the membranes probed with phosphotyrosine antibody (FIG. 15). Mim-1 treatment stimulated changes in phosphotyrosine content of at least four proteins (arrows indicated) ranging in molecular weight from 40–80 kDa. The effects of mim-1 on changes in phosphotyrosine content are concentration dependent, being maximal between 0.5 and 1 mim-1. The most striking change is the doublet indicated by the top arrow (FIG. 15), running a t 60–65 kDa. The concentration dependent differences between the mim-1 necessary to stimulate migration of mesenchymal cells are between five- and ten-fold lower than those necessary to stimulate changes in tyrosine phosphorylation. While the apparent changes in phosphotyrosine do not appear dramatic, the protein with the most anemic response is identified (FIG. 15, bottom arrow). This represents a wide range in concentration of mim-1 to which the osteoblasts will respond (2 µg/ml is approximately 55 nM).

Figure 16:
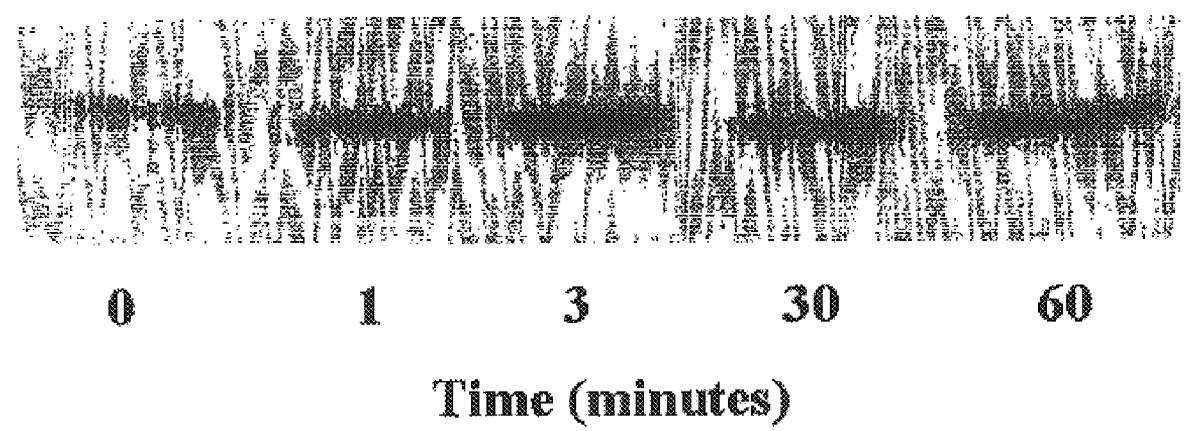
FIG. 16 shows the effect of time of mim-1 treatment on p42/p44 MAP kinase activation in mesenchymal cells. Cells were treated with 2 µg/ml of purified mim-1 for the indicated times, washed, lysed and 25 µg protein resolved on 10% SDS PAGE. Protein was transferred to PVDF membrane and the membranes probed with phospho-specific p42/p44 MAP kinase antibody (New England Biolabs).

Mim-1 also stimulated the increased p42/44 MAP-kinase phosphorylation in a time-dependent manner in MG63 cells. The time dependence of mim-1 activation of MAP kinase by Western analysis with the phospho specific MAP kinase antibody was tested. This antibody detects only the phosphorylated (activated) form of MAP kinase (FIG. 16). Mim-1 stimulates the time dependent activation of MAP kinase with maximal effects at 3 minutes (compare this with 2 µg/ml in FIG. 15). The concentration dependence for activation of MAP kinase was maximal at 1–2 µg/ml (not shown) similar to the effects of mim-1 on tyrosine phosphorylation (FIG. 15).

Figure 17A:
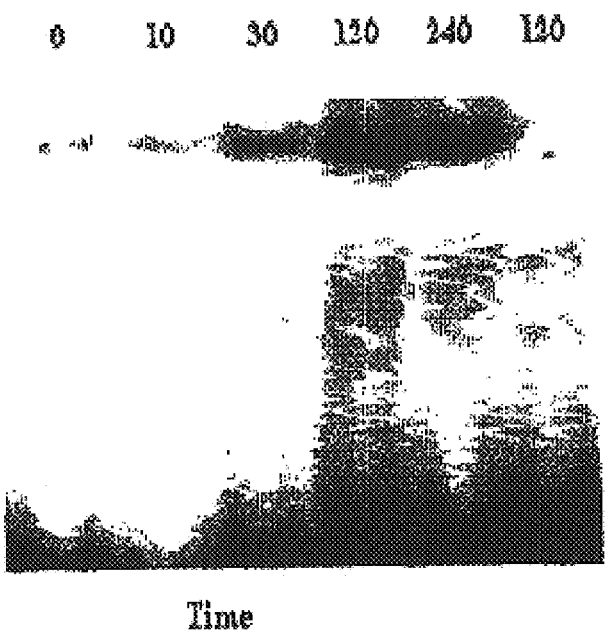
FIG. 17A show cells treated with 2 µg/ml of purified mim-1 for 0, 10, 30, 60, 120, and 240 min washed, lysed and nuclear extracts prepared. A 27 bp oligonucleotide from the osteocalcin proximal cbfa1 binding site was 5' end labeled with $\gamma^{32}$P-ATP by T4 kinase. Equivalent amounts of nuclear extracts were incubated with the probe for 30 min and samples resolved on a 5% gel, fixed, dried and binding visualized by autoradiography. Specific binding is demonstrated in 120 min extract with 100× excess unlabeled probe (Lane 6).
Figure 17B:
FIG. 17B shows MG63 cells treated with the indicated concentrations (µg/ml) of mim-1 for 2 hrs and mobility shifts done as in FIG. 17A.

After showing acute activation of the MAP kinase-signaling pathway in osteoblasts by mim-1, the role of mim-1 in osteoblast differentiation was investigated. FIG. 17 shows mim-1 stimulated the binding of osteoblast specific transcription factor, cbfa1, to both osteocalcin and osteoprotegrin promoters (only osteocalcin shown, FIG. 17). In electrophoretic mobility shift assays (EMSA), mim-1 stimulated increased cbfa1 binding to labeled oligonucleotides from the proximal cbfa1-binding site in the osteocalcin promoter (FIG. 17) in a time (FIG. 17A) and concentration dependent manner (FIG. 17B). Mim-1 treatment (2 µg/ml) of MG63 cells resulted in a nearly five-fold increase in binding of the cbfa1 transcription factor to the osteocalcin oligonucleotide probe. Binding was maximal at 2 hours treatment and decreased ~30% by 4 hours (FIG. 17; compare 120 and 240 min). In addition, binding (first 120 min lane) was blocked b y addition of 100-fold excess unlabeled oligonucleotide (Panel A, last lane), indicating specific binding. The mim-1 concentration dependence of mim-1 stimulated cbfa1 binding was nearly 2-fold above the control levels in response to 20 ng/ml, or 5–10 fold lower concentration as necessary to stimulate changes in tyrosine phosphorylation. However this concentration dependence is similar to that observed to stimulate osteoblast precursor cell migration. The data from FIGS. 14–16 indicate that mim-1 stimulates rapid and early events in osteoblast differentiation and that mim-1 is an osteoclast-derived osteoblast differentiation factor.

Figure 18A:
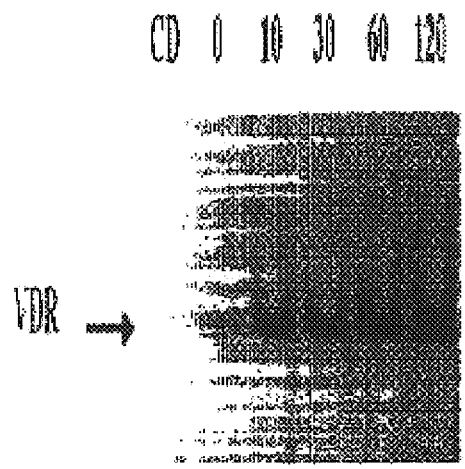
FIG. 18A shows $^{32}$P-labeled double-stranded oligonucleotide probe, corresponding to the VDRE from the human osteocalcin promoter, with T4 kinase and incubated with nuclear extracts from MG-63 cells treated with 2 µg/ml of mim-1 for 0, 10, 30, 60 and 120 minutes. Competitive displacement (CD) of vitamin D receptor interaction by 100× of cold probe.
Figure 18B:
FIG. 18B shows cells treated with mim-1 for 2 or 3 hrs and VDR/VDRE supershifted with a 1:5 or 1:10 dilution of VDR polyclonal antibody 4707. CD is competitive displacement as in FIG. 18A and NS is incubaton with 100× NonSpecific probe (vitellogenin estrogen response element), both were included as controls with 2 hr mim-1 extracts.
Figure 18B:
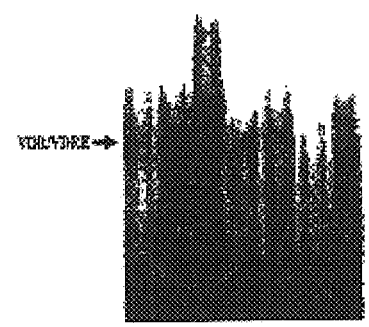
Figure 18C:
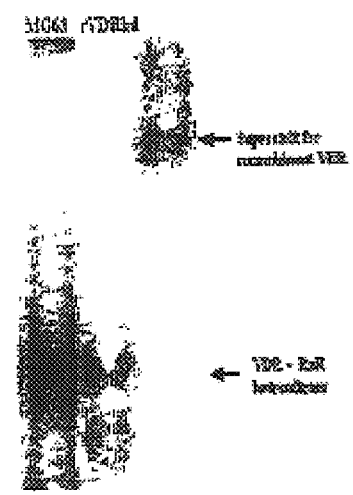
FIG. 18C shows VDR/VDRE from MG63 compared to recombinant VDR heterodimer (rVDRhd), both migrate with the same mobility, and the recombinant VDR/RXR is supershifted with the same antibody used in FIG. 18B.
Figure 19A:
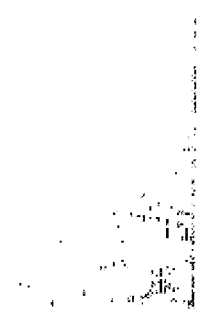
FIG. 19 shows mim-1 stimulates in vitro matrix mineralization by MC3T3-E1 cells. MC3T3-E1 cells ($2.5\times10^4$ cells/well) were cultured in DMEM/F12 plus 1% FBS in the presence of 10 mM glycerophosphate, 50 µg/ml ascorbic acid and either, 0, 3 or 15 nM (FIGS. 19A–C, respectively) of purified mim-1 for 16 days. Cells were VonKossa stained to demonstrate mineralized matrix. 200× magnification, data is representative of n=2 experiments. VonKossa staining was confirmed by measuring total calcium in each well. Calcium was acid hydrolyzed, neutralized and measured on a Kodak Ektachem DTSC II and the results illustrated in the bar graph at the right. Calcium measurements are representative single determinations from 2 separate experiments.
Figure 19B:
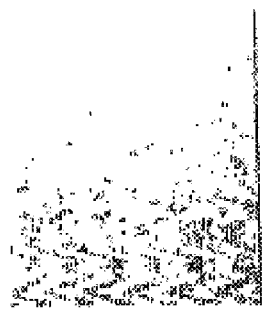
Figure 19C:
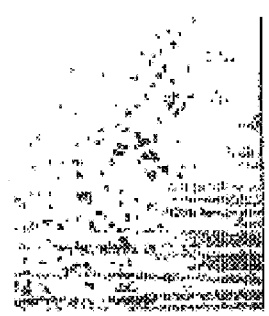
Figure 19C:
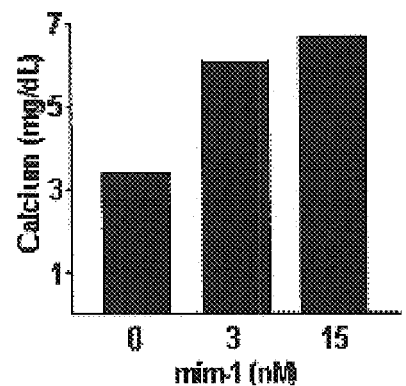

Cbfa binding to the osteocalcin promoter was selected because the promoter has numerous transcription factor and steroid receptor binding sites. Mim-1 was further tested to see if it stimulates multiple pathways favoring osteoblast differentiation. As vitamin D is often used to promote differentiation of osteoblasts, MG63 cells were treated with mim-1 and isolated nuclear extracts. Vitamin D receptor binding to the VDRE in the osteocalcin promoter was tested in electrophoretic mobility shift assays (FIG. 18). Mim-1 stimulated Vitamin D receptor binding to the VDRE in a time dependent manner in the absence of added 1.25 (OH)$_2$ D3 (unliganded binding) (FIG. 18A). Comparison of the time course of cbfa1 binding (FIG. 14) and VDR binding (FIG. 18) indicates that VDR binding the VDRE is more rapid (compare control verses 10 min) than cbfa1 binding. This suggests that mim-1 stimulates nongenomic effects through the vitamin D receptor.

As MAP kinase is known to be activated by mim-1 and reported to be calcium dependent and activated by vitamin D (70), the possibility of calcium involvement in mim-1 dependent signaling is next tested. Initial characterization indicates that the vitamin D receptor heterodimer (VDR/RXR) is supershifted with a polyclonal antibody to the vitamin D receptor (FIG. 18B), suggesting that mim-1 stimulates early events in osteoblast differentiation and may modulate hormonal regulation of osteoblast differentiation.

Mim-1 is tested to determine whether mim-1 would also support and stimulate long-term differentiation events of in vitro nodule formation and mineralization. The effects of mim-1 on matrix mineralization using MC3T3 E1 cells are shown in FIG. 19. Mim-1 stimulated a concentration dependent increase in mineralization of MC3T3-E1 cells with maximal effects at 0.5 µg/ml mim-1.

Figure 20:
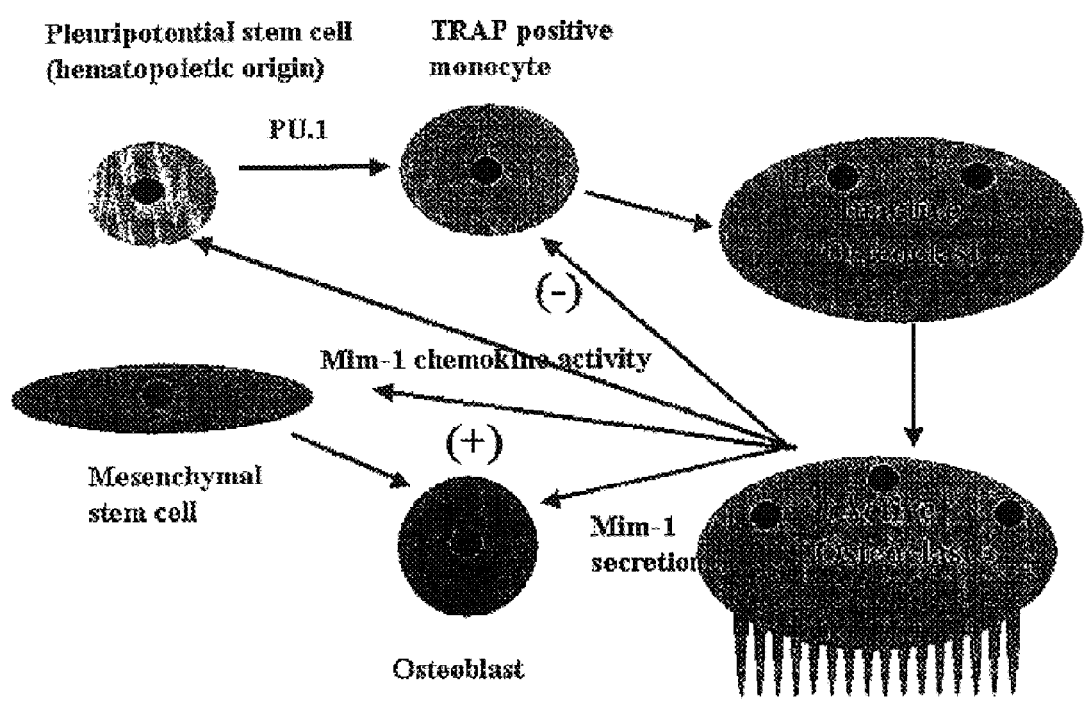
FIG. 20 shows the potential role of mim-1 in bone biology. Osteoclasts are derived from pleuripotential hematopoietic stem cells that express mim-1, while osteoblasts are derived from mesenchymal stem cells that do not express mim-1. Differentiation of osteoclast precursor cells requires RANKL on stromal cells in the presence of M-CSF. Secretion of the abundant mim-1 protein by osteoclasts may results in physiologically relevant concentrations of mim-1 in the bone microenvironment. Mim-1 may be important in regulating differentiation of osteoclast precursors, as well as modulating the recruitment, development and/or activity of osteoblast precursor cells, thus coordinating new bone synthesis in areas of recent bone resorption.

Mim-1 has high sequence homology with the neutrophil chemokine Lect2 and mim-1 has a dual purpose in bone. In addition to secretion being part of the mechanism to increase activity of osteoclasts, mim-1 serves to attract osteoblast precursor cells to areas of recent bone resorption, thereby coordinating bone remodeling (FIG. 20).

Figure 21:
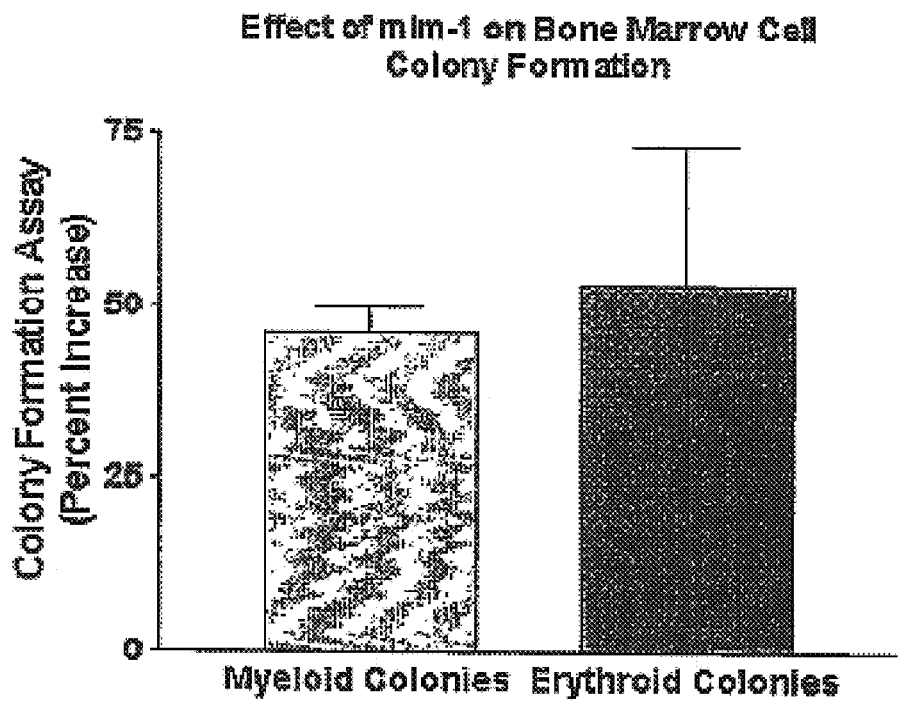
FIG. 21 shows that mim-1 stimulates colony formation by human bone marrow cells. Human bone marrow cells were cultured in IMDM with GM-CSF (50 ng/ml), IL3 (10 ng/ml) and 20 ng/ml SCF (controls) for 3 days –/+2 µg/ml mim-1 and analyzed by FACS analysis. The remaining cells were cultured in colony formation assays an additional 14 days with the same growth factors minus or plus 2 µg/ml mim-1. Data is the average –/+SEM of 3 separate experiments.

Mim-1 is a chemokine that is secreted into the bone microenvironment. Mim-1 is therefore likely to get into the general circulation. To test the effects mim-1 has on other cells in the bone microenvironment as well as cells outside this bone microenvironment, human bone marrow cell cultures were stimulated by mim-1 . An increase in the proportion of cells that are CD14$^+$ as determined by FACS analysis was observed. These cells were then cultured in soft agar assays in the presence of IL3 and SCF (control cells). Mim-1 stimulates an approximately 50% increase in both myeloid and erythroid cell colony formation (FIG. 21).

Figure 22:
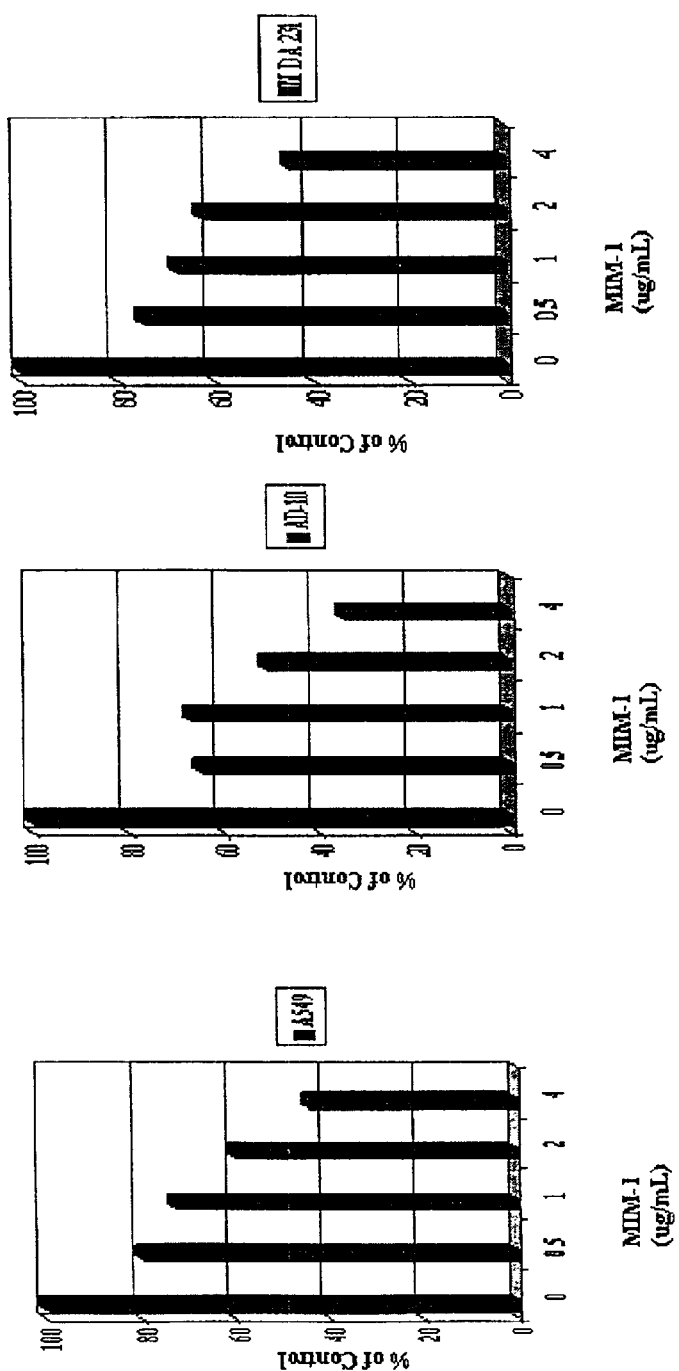
FIG. 22 shows that mim-1 inhibits cell growth of three different human cancer cell lines in a concentration dependent manner. Cancer cells (A549, lung cancer; MDA231, Breast cancer; and AD10, ovarian cancer) were cultured for three days in the presence of the indicated concentrations of mim-1. Cells were counted in 10 random grids, and the data is plotted as Percent of Control (no added mim-1). Data are representative of 2 separate experiments.

The effects of mim-1 on the growth of three human cancer cell lines were also tested. A concentration dependent inhibition of cell growth by mim-1 was shown (FIG. 22).

Discussion

Regulation of bone mass is a complex process requiring tight regulation of the cellular activity of both osteoclasts and osteoblasts. This tight regulation necessitates an intricate and dynamic coordination of cellular signals. It has long been speculated that a wide variety of molecules including neuropeptides (29), IL-6 (30), osteoprotegrin (7, 31), parathyroid hormone (32), TGFβ (33), prostaglandins (34) and osteopontin (35), to name a few, are important mediators of cellular signaling between osteoclasts and osteoblasts. Much attention has also been focused on signaling between osteoblasts and osteoclasts (13, 36, 37).

Many factors are involved in recruiting precursor cells of osteoblast or osteoclast lineage. It would seem especially important for osteoclasts to have a mechanism to stimulate recruitment of osteoblastic precursors. Such a pathway would allow for coordinated remodeling of bone. Secretion of an abundant cellular protein, which is important in maintaining the balance between bone degradation and bone synthesis, by either osteoblasts or osteoclasts has not been reported. Secretion of an abundant osteoclastic protein may be necessary to attain physiologically relevant concentrations of a 35 kDa protein in the bone microenvironment.

A 35 kDa osteoclast protein, mim-1, was unambiguously identified that is secreted in a time dependent manner. Mim-1 secretion is correlated with increased osteoclast activity when stimulated by PMA (FIG. 3). Mim-1 was originally cloned from chicken marrow promyelocytes (15). In these cells mim-1 was very abundant, consistent with the observation in osteoclasts. There is no known function described for mim-1 (15) and thus its potential role in osteoclast or osteoblast biology is not readily apparent. However, mim-1 and a 16 kD protein (Lect2) that has sequence homology with mim-1 are both reported to be secreted proteins (15, 38, 39). Interestingly, Lect2 (also known as chondromodulin II (40)) has chemokine activity, having been shown to attract neutrophils (38, 39) and stimulate osteoblast proliferation (41). Mim-1 was speculated to have some function in the milieu of bone marrow, or to possibly serve as a structural protein in granules where it is localized (15). The present data indicates that mim-1 is secreted by isolated osteoclasts under basal conditions since mim-1 accumulates in media over a four-day incubation in culture (FIG. 6). However, mim-1 secretion is rapidly increased in response to PMA treatment of osteoclasts (FIG. 5). The PMA stimulated increase in bone resorption is inhibited by the calmodulin antagonists, tamoxifen and trifluoperazine. The PMA concentration dependent increase in bone resorption is paralleled by an increase in calmodulin protein levels. In addition, the calmodulin antagonists inhibit both the PMA dependent increase in bone resorption and calmodulin levels. In contrast, the calmodulin antagonists did not inhibit the secretion of mim-1.

Analysis of mim-1 sequence demonstrates two imperfect direct repeat sequences of 136 amino acids linked together by a 14 amino acid tether. In the 136 amino acid repeat sequences only 30 amino acids are non-identical (77% identity) and most of the 30 non-identical sites have conservative substitutions. Lect2/chondromodulin II (38, 39), has high sequence homology with the repeat structure in mim-1 but is a 16 kD protein isolated from human T-cells, that is expressed primarily in liver and is a distinct gene product from mim-1 (40).

The majority of previous investigations of the mim-1 protein involved transcriptional regulation of mim-1 gene expression (15). Northern blot analysis indicated that bone marrow is the tissue with the only detectable expression of mim-1 and that mim-1 was localized in promyelocytes but was not expressed in brain, heart, lung, kidney, liver, muscle, thymus, bursa or spleen (15). Transcriptional regulation of mim-1 expression is governed by the transcription factor myb. Myb activity in regulating mim-1 expression is reported to undergo synergistic activation with C/EBP (42, 43). Interestingly, transcriptional regulation of mim-1 expression is negatively regulated by PU. 1 which has been previously been reported to be necessary for osteoclast differentiation (44). In fact PU.1 knockouts are osteopetrotic (43), while neutrophils deficient in PU.1 fail to differentiate (45). In addition, myb knockouts are embryonic lethals due to a failure of hepatic hematopoiesis (46). Furthermore, there is a negative correlation between expression of mim-1 and cell differentiation (15).

Mim-1 was first identified in promyelocytes and is abundant in freshly isolated osteoclasts (FIGS. 2, 5, and 8), which are reported to be derived from promyelocytes in the presence of stromal cells (47, 48). This, together with the fact that mim-1 is secreted preceding a 4-fold stimulation of osteoclastic bone resorption by PMA, suggest that mim-1 may have paracrine effects on osteoclast differentiation. In addition, due to the high sequence homology with the neutrophil chemokine Lect2, mim-1 may have a dual purpose in bone. In addition to secretion being part of the mechanism to increase activity of osteoclasts, mim-1 may also serve to attract osteoblast precursor cells to areas of recent bone resorption, thereby being a mechanism involved in coordinating bone remodeling (FIG. 20).

With mim-1 secreted into the bone microenvironment as a chemokine, it is likely to get into general circulation, so there is the potential for mim-1 to have effects on other cells in the bone microenvironment as well as cells not in bone. The effects of mim-1 on human bone marrow cell cultures were demonstrated with mim-1 stimulating an increase in the proportion of cells that are $CD14^+$ as determined by FACS analysis and there was about a 50% increase in both myeloid and erythroid cell colony formation (FIG. 21).

Lastly, mim-1 also demonstrated a concentration dependent inhibition of three human cancer cell lines (FIG. 22).

The following references were cited herein:
1. Suda, T., Takahashi, N., and Martin, T. J. (1992) Endocrine Rev. 13: 66–68.
2. Fujikawa, Y., Quinn, J. M. W., Sabokar, A., McGee, Jo'D., and Athanasou, N. A. (1996) Endocrinology 137: 4058–4060.
3. Udagawa, N., Takahashi, N., Akatsu, T., Tanaka, H., Sasaki, T., Nishihara, T., Martin, T., and Suda, T. (1990) Proc. Natl. Acad. Sci. USA 87:7260–7264.
4. Tanaka, S., Takahashi, N., Udagawa, N., Tamura, T., Akatsu, T., Stanley, E., Kurokawa, T., and Suda, T. (1993) J. Clin. Invest. 91: 257–263.
5. Yasuda, H., Sjhima, N., Nakagawa, N., Yamaguchi, K., Kinosaki, M., Mochizuki, S., Tomoyasu, A., Yano, K., Goto, M., Murakami, A., Tsuda, E., Morinaga, T., Higashio, K., Udagawa, N., Takahashi, N., and Suda, T. (1998) Proc. Natl. Acad. Sci. USA. 95: 3597–3602.
6. Wani, M. R., Fulle, K., Kim, N. S., Choi, Y., and Chambers, T. (1999) Endocrinology 140:1927–1935.
7. Simonet, W. S., Lacey, D. L., Dunstan, C. R., Kelley, M., Chang, M -S., Luthy, R., Nguyen, H. Q., Wooden, S., Bennett, L., Boone, T., Shimamoto, G., DeRose, M., Elliot, R., Columbero, A., Tan, H.-L., Trail, G., Sullivan, J., Davy, E., Bucay, N., Renshaw-Gegg, L., Hughes, T. M., Hill, D., Pattison, W., Campbell, P., Sanders, S., Van, G., Tarpley, J., Derby, P., Lee, R., Program, A. E., and Boyle, W. J. (1997) Cell 89: 309–319.
8. Wong, B. R., Rho, J., Robinson, E., Orlinick, J., Chao, M., Kalachikov, S., Cayani, E., Bartlett III, F. S., Frankel, W. N., Lee, S. Y., and Choi, Y. (1997) J. Biol. Chem. 272: 25190–27194.
9. Horowitz, M. C. (1998) J. Clin. Densitometry 1: 187–198.
10. Menaa, C., Devlin, R. D., Reddy, S. V., Gazitt, Y., Choi, S. J., and Roodman, G. D. (1999) J. Clin. Invest. 103: 1605–1613.
11. Ohsaki, Y., Takahashi, S., Scarcez, T., Demulder, A., Nishihara, T., Williams, R., and Roodman, G. D. (1992) Endocrinology 131: 2229–2234.
12. Oursler, M. J. (1994) J. Bone Miner. Res. 9: 443–452.
13. Manolagas S. C., and Weinstein R. S. (1999) J. Bone Miner. Res. 14: 1061–1066.
14. Fuller, K, Owens, J. M., and Chambers, T. J. (1998) J. Endocrinol. 158: 341–350.
15. Ness, S. A., Marknell, A., and Graf, T. (1989) Cell 59: 1115–1125.
16. Blair, H. C., Kahn, A. J., Crouch, E. C, Jeffrey, J. J., and Teitelbaum, S. L., (1986) J. Cell Biol. 102:1164–1172.
17. Williams, J. P., Blair, H. C., McKenna, M. A., Jordan S. E., and McDonald, J. M.(1996) J. Biol. Chem. 271: 12488–12495.

18. Teitelbaum, S. L., Stewart, C. C., and Kahn, A. J. (1979) Calcif Tissue Int. 27: 255–261.
19. Carano, A., Schlesinger, P. H., Athanasou, N. A., Teitelbaum, S. L., and Blair, H. C. (1993) Am J. Physiol. 264: C694–C701.
20. Dong, S. S., Williams, J. P., Jordan, S. E., Van Epps-Fung, C., Cornwell, T., Blair, H. C. (1999) J. Cell. Biochem. 73: 478–487.
21. Towbin, H., Staehelin, T., Gordon, J. (1979) Proc. Natl. Acad. Sci. USA 76: 4350–4354.
22. Hellman, U., Wernstedt, C., Gonez, J., and Heldin, C.-H. (1995) Anal. Biochem. 224: 451–455.
23. Jeno, P., Mini, T., Moes, S., Hintermann, E. and Horst, M. (1995) Anal. Biochem. 224: 75–82.
24. Davis, M. T., and Lee, T. D. (1998) J. Am. Soc. Mass Spectrometry 9: 194–201.
25. Moore, R. E., Licklider, L., Schumann, D., and Lee, T. D. (1998). Anal. Chem. 70: 4879–4884.
26. Eng, J. K., McCormack, A. L., Yates, J. R. (1995) J. Am. Soc. Mass Spectrom. 5: 976–989.
27. Williams J. P., McKenna M. A., Thames A. M., and McDonald J. M. (2000) Tamoxifen inhibits phorbol ester stimulated osteoclastic bone resorption: an effect mediated by calmodulin. *Biochemistry and Cell Biology;* 78:715–723.
28. Morelli, S., Buitrago, C., Boland R., and Boland A. R. (2001) The stimulation of MAP kinase by 1, 24(OH)$_2$-vitamin D(3) in skeletal muscle cells is mediated by protein kinase C and calcium. Mol. Cell. Endocrinol. 173: 41–52.
29. Konttinen, Y., Imai, S., and Suda, A. (1996) Acta Orthopaedica Scandinavica 67: 632–639.
30. Manolagas, S. C. (1998) Annals of the New York Academy of Sciences 840:194–204.
31. Lacey, D. L., Timms, E., Tan, H.-L., Kelley, M. J., Dunstan, C. R., Burgess, T., Elliott, R., Colombero, A., Elliott, G., Scully, S., Hsu, H., Sullivan, J., Hawkins, N., Davy, E., Capparelli, C, Eli, A., Qian, Y.-X, Kaufamn, S., Sarosi, I., Shalhoub, V., Senaldi, G., Guo, J., Delaney, J., and Boyle, W. J. (1998) Cell 93: 165–176.
32. Partridge, N. C, Bloch, S. R., and Pearman, A. T. (1994) J. Cell. Biochem. 55: 314–327.
33. Duivenvoorden, W. C., Hirte, H. W., and Singh, G. (1999) Clinical & Experimental Metastasis 17: 27–34.
34. Kawaguchi, H., Pilbeam, C. C., Harrison, J. R., and Raisz, L. G. (1995) Clinical Orthopaedic & Related Res. 313: 36–46.
35. Yamata, T., Mocharla, H., Taguchi, Y., Igietseme, J. U., Manolagas, S. C, and Abe, E. (1997) Endocrinology 138: 3047–3055.
36. Kahn, A. J., and Partridge, N. C. (1987) Am. J. Otolaryngol. 8: 258–264.
37. Aurbach, G. H., Marx, S. J. and Spiegal, A. M. (1985) in Williams' Textbook of Endocrinology (Wilson J D and Foster D W eds.) 7$^{th}$ Ed., pp. 1173–1174, W B Saunders Co., Philadelphia.
38. Yamagoe, S., Akasaka, T., Uchida, T., Hachiya, T., Okabe, T., Yamakawa, Y., Arai, T., Mizuno, S., and Suzuki, K. (1997) Biochem. Biophys. Res. Commun. 237: 116–120.
39. Yamagoe, S., Yamakawa, Y., Matsuo, Y., Minowada, J., Mizuno, S., and Suzuki, K. (1996) Immunol. Lett. 52: 9–13.
40. Shukunami, C., Konodo, J., Wakai, H., Takahashi, K., Inoue, H., Kamizono, A. and Hiraki, Y. (1998) J. Biochem. 125: 436–442.
41. Mori, Y., Hiraki, Y., Shukunami C., Kakudo, S., Shiokawa, M., Kagoshima, M., Mano, H., Hakeda, Y., Kurokawa, T., Suzuki, F., and Kumegawa, M. (1997) FEBS Letters 406: 310–314.
42. Burk, O., Mink, S., Ringwald, M., and Klempnaur, K. H. (1993) The EMBO Journal 12: 2027–2038.
43. Oelgeschlager, M., Janknecht, R., Krieg, J., Schreek, S., and Luscher, B. (1996) Interaction of the co-activator CBP with Myb proteins: effects on myb-specific transactivation and on the cooperativity with NF-M. The EMBO Journal 17: 2771–2780.
44. Tondravi, M. M., McKercher, S. R., Anderson, K., Erdmann, J. M., Quiroz, M., Maki, R, and Teitelbaum, S. L. (1997) Nature: 386:81–84.
45. Anderson, K. L., Smith, K. A., Pio, F., Torbett, B. E., and Maki, R. A. (1998) Blood 92: 1576–1585.
46. I.-H., and Reddy, E. P. (1999) Oncogene 18: 3017–3033.
47. Nutt, S. L., Heavy, B., Rollink, A. G., Busslinger, M. (1999). Nature 401: 556–562.
48. Rolink, A. G., Nutt, S. L., Melcher, F., and Busslinger, M. (1999) Nature 401: 603–606.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of increasing the proportion of $CD14^+$ cells derived from bone marrow cells, comprising the step of:

administering to said bone marrow cells a pharmacologically effective dose of a pharmaceutical composition comprising the myb induced myeloid protein-1 (mim-1) of SEQ ID NO: 8, a biologically active fragment of SEQ ID NO: 8, or a fusion protein containing a biologically active fragment of SEQ ID NO: 8, wherein said mim-1 or fragment thereof increases the proportion of $CD14^+$ cells derived from said bone marrow cells.

2. The method of claim 1, wherein said pharmaceutical composition is administered in a dose of about 30 nM.

* * * * *

SEQUENCE LISTING

```
<160> NUMBER OF SEQ ID NOS: 14

<210> SEQ ID NO 1
<211> LENGTH: 10
<212> TYPE: PRT
<213> ORGANISM: Gallus gallus
<220> FEATURE:
<222> LOCATION: 200..209
<223> OTHER INFORMATION: amino acid sequence tryptic peptide from
      mim-1 protein
```

```
<400> SEQUENCE: 1

Tyr Gly Cys Gly Tyr Phe Gly Ala Pro Arg
                5                   10

<210> SEQ ID NO 2
<211> LENGTH: 8
<212> TYPE: PRT
<213> ORGANISM: Gallus gallus
<220> FEATURE:
<222> LOCATION: 116..123
<223> OTHER INFORMATION: amino acid sequence tryptic peptide from
      mim-1 protein

<400> SEQUENCE: 2

Leu Val Cys Ile His Pro Ile Arg
                5

<210> SEQ ID NO 3
<211> LENGTH: 15
<212> TYPE: PRT
<213> ORGANISM: Gallus gallus
<220> FEATURE:
<222> LOCATION: 94..108
<223> OTHER INFORMATION: amino acid sequence tryptic peptide from
      mim-1 protein

<400> SEQUENCE: 3

Phe Phe His Asn Gly Asn Ser Ile Asp Asp Gly Val Gln Ile Arg
                5                   10                  15

<210> SEQ ID NO 4
<211> LENGTH: 8
<212> TYPE: PRT
<213> ORGANISM: Gallus gallus
<220> FEATURE:
<222> LOCATION: 266..273
<223> OTHER INFORMATION: amino acid sequence tryptic peptide from
      mim-1 protein

<400> SEQUENCE: 4

Leu Leu Cys Ile His Pro Ile Arg
                5

<210> SEQ ID NO 5
<211> LENGTH: 22
<212> TYPE: PRT
<213> ORGANISM: Gallus gallus
<220> FEATURE:
<222> LOCATION: 94..115
<223> OTHER INFORMATION: amino acid sequence tryptic peptide from
      mim-1 protein

<400> SEQUENCE: 5

Phe Phe His Asn Gly Asn Ala Ile Asp Asp Gly Val Gln Ile Ser
                5                   10                  15

Gly Ser Gly Tyr Cys Val Lys
                20

<210> SEQ ID NO 6
<211> LENGTH: 16
<212> TYPE: PRT
<213> ORGANISM: Gallus gallus
<220> FEATURE:
<222> LOCATION: 293..308
<223> OTHER INFORMATION: amino acid sequence tryptic peptide from
      mim-1 protein

<400> SEQUENCE: 6
```

-continued

Val Phe Pro Gly Ile Ile Ser His Ile His Val Glu Asn Cys Asp
                5                  10                  15

Arg

<210> SEQ ID NO 7
<211> LENGTH: 25
<212> TYPE: PRT
<213> ORGANISM: Gallus gallus
<220> FEATURE:
<222> LOCATION: 219..243
<223> OTHER INFORMATION: amino acid sequence tryptic peptide from
      mim-1 protein

<400> SEQUENCE: 7

Gly Val Asp Val Ile Cys Ala Asp Gly Ala Thr Val Tyr Ala Pro
                5                  10                  15

Phe Ser Gly Glu Leu Ser Gly Pro Val Lys
                20                  25

<210> SEQ ID NO 8
<211> LENGTH: 326
<212> TYPE: PRT
<213> ORGANISM: Gallus gallus
<220> FEATURE:
<223> OTHER INFORMATION: amino acid sequence of mim-1 protein

<400> SEQUENCE: 8

Met Pro Ala Leu Ser Leu Ile Ala Leu Leu Ser Leu Val Ser Thr
                5                  10                  15

Ala Phe Ala Arg Gln Trp Glu Val His Pro Gln Gln Gln Gly
                20                  25                  30

Arg His Trp Ala Gln Ile Cys Ser Gly Asn Pro Phe Asn Arg Ile
                35                  40                  45

Arg Gly Cys Asp Arg Tyr Gly Cys Gly Asn Tyr Gly Ala Ser Arg
                50                  55                  60

Gln Gly Lys Gly Glu Lys His Lys Gly Val Asp Val Ile Cys Thr
                65                  70                  75

Asp Gly Ser Ile Val Tyr Ala Pro Phe Trp Gly Gln Leu Ser Gly
                80                  85                  90

Pro Ile Arg Phe Phe His Asn Gly Asn Ala Ile Asp Asp Gly Val
                95                  100                 105

Gln Ile Ser Gly Ser Gly Tyr Cys Val Lys Leu Val Cys Ile His
                110                 115                 120

Pro Ile Arg Tyr His Gly Gln Ile Gln Lys Gly Gln Gln Leu Gly
                125                 130                 135

Arg Met Leu Pro Met Gln Lys Val Phe Pro Gly Ile Val Ser His
                140                 145                 150

Ile His Val Glu Asn Cys Asp Gln Ser Asp Pro Thr His Leu Leu
                155                 160                 165

Arg Pro Ile Pro Asp Ile Ser Pro Pro Phe Pro Gln Gln Asp Ala
                170                 175                 180

His Trp Ala Val Val Cys Ala Gly Asn Pro Thr Asn Glu Ile Arg
                185                 190                 195

Gly Cys Lys Asp Tyr Gly Cys Gly Tyr Phe Gly Ala Pro Arg Arg
                200                 205                 210

Asn Gly Lys Gly Glu Lys His Lys Gly Val Asp Val Ile Cys Ala
                215                 220                 225

```
Asp Gly Ala Thr Val Tyr Ala Pro Phe Ser Gly Glu Leu Ser Gly
                230                 235                 240

Pro Val Lys Phe Phe His Asn Gly Asn Ala Ile Asp Asp Gly Val
                245                 250                 255

Gly Ile Arg Gly Ser Gly Phe Cys Val Lys Leu Leu Cys Ile His
                260                 265                 270

Pro Ile Arg Tyr Asn Gly Arg Ile Ser Lys Gly Gln Val Leu Gly
                275                 280                 285

Arg Met Leu Pro Met Gln Arg Val Phe Pro Gly Ile Ile Ser His
                290                 295                 300

Ile His Val Glu Asn Cys Asp Arg Ser Asp Pro Thr Ser Asn Leu
                305                 310                 315

Glu Arg Gly Lys Gly Glu Ser Glu Met Glu Val
                320                 325

<210> SEQ ID NO 9
<211> LENGTH: 113
<212> TYPE: PRT
<213> ORGANISM: unknown
<220> FEATURE:
<222> LOCATION: 38..165
<223> OTHER INFORMATION: amino acid sequence of region of Lect2
      protein homologous to repeat sequences of N
      and C terminal ends of the mim-1 protein

<400> SEQUENCE: 9

Tyr Gly Cys Gly Gln Tyr Ser Ala Gln Arg Thr Gln Arg His His
                  5                  10                  15

Pro Gly Val Asp Val Leu Cys Ser Asp Gly Ser Val Val Tyr Ala
                 20                  25                  30

Pro Phe Thr Gly Lys Ile Val Gly Gln Glu Lys Pro Tyr Arg Asn
                 35                  40                  45

Lys Asn Ala Ile Asn Asp Gly Ile Arg Leu Ser Gly Arg Gly Phe
                 50                  55                  60

Cys Val Lys Ile Phe Tyr Ile Lys Pro Ile Lys Tyr Lys Gly Ser
                 65                  70                  75

Ile Lys Lys Gly Glu Lys Leu Gly Thr Leu Leu Pro Leu Gln Lys
                 80                  85                  90

Ile Tyr Pro Gly Ile Gln Ser His Val His Val Glu Asn Cys Asp
                 95                 100                 105

Ser Ser Asp Pro Thr Ala Tyr Leu
                110

<210> SEQ ID NO 10
<211> LENGTH: 115
<212> TYPE: PRT
<213> ORGANISM: Gallus gallus
<220> FEATURE:
<222> LOCATION: 51..165
<223> OTHER INFORMATION: amino acid sequence of repeat sequence of N
      terminal end of mim-1 protein homologous
      to Lect2 protein

<400> SEQUENCE: 10

Tyr Gly Cys Gly Asn Tyr Gly Ala Ser Arg Gln Gly Lys Gly Glu
                  5                  10                  15

Lys His Lys Gly Val Asp Val Ile Cys Thr Asp Gly Ser Ile Val
                 20                  25                  30

Thr Ala Pro Phe Ser Gly Gln Leu Ser Gly Pro Ile Arg Phe Phe
                 35                  40                  45
```

-continued

```
His Asn Gly Asn Ala Ile Asp Asp Gly Val Gln Ile Ser Gly Ser
            50                  55                  60

Gly Phe Cys Val Lys Leu Leu Cys Ile His Pro Ile Arg Tyr Asn
            65                  70                  75

Gly Arg Ile Ser Lys Gly Gln Val Leu Gly Arg Met Leu Pro Met
            80                  85                  90

Gln Arg Val Phe Pro Gly Ile Ile Ser His Ile His Val Glu Asn
            95                 100                 105

Cys Asp Arg Ser Asp Pro Thr Ser Asn Leu
           110                 115

<210> SEQ ID NO 11
<211> LENGTH: 115
<212> TYPE: PRT
<213> ORGANISM: Gallus gallus
<220> FEATURE:
<222> LOCATION: 200..315
<223> OTHER INFORMATION: amino acid sequence of repeat sequence of C
      terminal end of mim-1 protein homologous
      to Lect2 protein

<400> SEQUENCE: 11

Thr Gly Cys Gly Tyr Phe Gly Ala Pro Arg Asn Gly Lys Gly Glu
             5                  10                  15

Lys His Lys Gly Val Asp Val Ile Cys Ala Asp Gly Ala Thr Val
            20                  25                  30

Tyr Ala Pro Phe Ser Gly Glu Leu Ser Gly Pro Val Lys Phe Phe
            35                  40                  45

His Asn Gly Asn Ala Ile Asp Asp Gly Val Gln Ile Arg Gly Ser
            50                  55                  60

Gly Tyr Cys Val Lys Leu Val Cys Ile His Pro Ile Arg Tyr His
            65                  70                  75

Gly Gln Ile Gln Lys Gly Gln Gln Leu Gly Arg Met Leu Pro Met
            80                  85                  90

Gln Lys Val Phe Pro Gly Ile Val Ser His Ile His Val Glu Asn
            95                 100                 105

Cys Asp Gln Ser Asp Pro Thr His Leu Leu
           110                 115

<210> SEQ ID NO 12
<211> LENGTH: 113
<212> TYPE: PRT
<213> ORGANISM: Gallus gallus
<220> FEATURE:
<223> OTHER INFORMATION: full length amino acid sequence of mim-1
      protein

<400> SEQUENCE: 12

Tyr Gly Cys Gly Gln Tyr Ser Ala Gln Arg Thr Gln Arg His His
             5                  10                  15

Pro Gly Val Asp Val Leu Cys Ser Asp Gly Ser Val Val Tyr Ala
            20                  25                  30

Pro Phe Thr Gly Lys Ile Val Gly Gln Glu Lys Pro Tyr Arg Asn
            35                  40                  45

Lys Asn Ala Ile Asn Asp Gly Ile Arg Leu Ser Gly Arg Gly Phe
            50                  55                  60

Cys Val Lys Ile Phe Tyr Ile Lys Pro Ile Lys Tyr Lys Gly Ser
            65                  70                  75
```

```
Ile Lys Lys Gly Glu Lys Leu Gly Thr Leu Leu Pro Leu Gln Lys
             80                  85                  90

Ile Tyr Pro Gly Ile Gln Ser His Val His Val Glu Asn Cys Asp
             95                 100                 105

Ser Ser Asp Pro Thr Ala Tyr Leu
            110
```

<210> SEQ ID NO 13
<211> LENGTH: 115
<212> TYPE: PRT
<213> ORGANISM: Gallus gallus
<220> FEATURE:
<223> OTHER INFORMATION: full length amino acid sequence of mim-1
      protein

<400> SEQUENCE: 13

```
Tyr Gly Cys Gly Asn Tyr Gly Ala Ser Arg Gln Gly Lys Gly Glu
              5                  10                  15

Lys His Lys Gly Val Asp Val Ile Cys Thr Asp Gly Ser Ile Val
             20                  25                  30

Tyr Ala Pro Phe Ser Gly Gln Leu Ser Gly Pro Ile Arg Phe Phe
             35                  40                  45

His Asn Gly Asn Ala Ile Asp Asp Gly Val Gln Ile Ser Gly Ser
             50                  55                  60

Gly Phe Cys Val Lys Leu Leu Cys Ile His Pro Ile Arg Tyr Asn
             65                  70                  75

Gly Arg Ile Ser Lys Gly Gln Val Leu Gly Arg Met Leu Pro Met
             80                  85                  90

Gln Arg Val Phe Pro Gly Ile Ile Ser His Val His Val Glu Asn
             95                 100                 105

Cys Asp Ser Ser Asp Pro Thr Ala Tyr Leu
            110                 115
```

<210> SEQ ID NO 14
<211> LENGTH: 115
<212> TYPE: PRT
<213> ORGANISM: Gallus gallus
<220> FEATURE:
<223> OTHER INFORMATION: full length amino acid sequence of mim-1
      protein

<400> SEQUENCE: 14

```
Tyr Gly Cys Gly Tyr Phe Gly Ala Pro Arg Asn Gly Lys Gly Glu
              5                  10                  15

Lys His Lys Gly Val Asp Val Ile Cys Ala Asp Gly Ala Thr Val
             20                  25                  30

Tyr Ala Pro Phe Ser Gly Glu Leu Ser Gly Pro Val Lys Phe Phe
             35                  40                  45

His Asn Gly Asn Ala Ile Asp Asp Gly Val Gln Ile Arg Gly Ser
             50                  55                  60

Gly Tyr Cys Val Lys Leu Val Cys Ile His Pro Ile Arg Tyr His
             65                  70                  75

Gly Gln Ile Gln Lys Gly Gln Gln Leu Gly Arg Met Leu Pro Met
             80                  85                  90

Gln Lys Val Phe Pro Gly Ile Val Ser His Ile His Val Glu Asn
             95                 100                 105

Cys Asp Gln Ser Asp Pro Thr His Leu Leu
            110                 115
```